United States Patent
Hasegawa et al.

(10) Patent No.: US 10,329,480 B2
(45) Date of Patent: Jun. 25, 2019

(54) SHEET INTEGRATED RARE EARTH COMPLEX AND USE THEREOF

(71) Applicant: National University Corporation Hokkaido University, Sapporo-shi, Hokkaido (JP)

(72) Inventors: Yasuchika Hasegawa, Sapporo (JP); Shiori Tateno, Sapporo (JP); Takayuki Nakanishi, Sapporo (JP); Koji Fushimi, Sapporo (JP)

(73) Assignee: National University Corporation Hokkaido University, Sapporo-shi, Hokkaido (JP)

( * ) Notice: Subject to any disclaimer, the term of this patent is extended or adjusted under 35 U.S.C. 154(b) by 0 days.

(21) Appl. No.: 14/902,933

(22) PCT Filed: Jul. 4, 2014

(86) PCT No.: PCT/JP2014/067909
§ 371 (c)(1),
(2) Date: Jan. 5, 2016

(87) PCT Pub. No.: WO2015/002295
PCT Pub. Date: Jan. 8, 2015

(65) Prior Publication Data
US 2016/0160121 A1   Jun. 9, 2016

(30) Foreign Application Priority Data
Jul. 5, 2013  (JP) .................................. 2013-141995

(51) Int. Cl.
| | |
|---|---|
| *C07F 9/53* | (2006.01) |
| *C07F 9/6521* | (2006.01) |
| *C07F 5/00* | (2006.01) |
| *C08L 101/00* | (2006.01) |
| *C09K 11/06* | (2006.01) |
| *H01L 51/50* | (2006.01) |
| *C07F 9/60* | (2006.01) |
| *H01L 51/00* | (2006.01) |
| *C07F 9/6596* | (2006.01) |
| *C09D 5/22* | (2006.01) |

(Continued)

(52) U.S. Cl.
CPC .............. *C09K 11/06* (2013.01); *C07F 5/003* (2013.01); *C07F 9/5329* (2013.01); *C07F 9/58* (2013.01); *C07F 9/60* (2013.01); *C07F 9/6521* (2013.01); *C07F 9/6596* (2013.01); *C08L 101/00* (2013.01); *C09D 5/22* (2013.01); *C09D 11/00* (2013.01); *H01L 51/0089* (2013.01); *C09K 2211/1007* (2013.01); *C09K 2211/1011* (2013.01); *C09K 2211/1014* (2013.01); *C09K 2211/1029* (2013.01); *C09K 2211/1059* (2013.01); *C09K 2211/1416* (2013.01); *C09K 2211/1425* (2013.01); *C09K 2211/1433* (2013.01); *C09K 2211/182* (2013.01); *C09K 2211/188* (2013.01); *H01L 51/5012* (2013.01); *H01L 51/5016* (2013.01)

(58) Field of Classification Search
CPC ............ C07F 9/53; C07F 9/6521; C07F 5/00; C09K 11/06; H01L 51/50; C08L 101/00
USPC .................. 544/181, 214; 546/2, 22; 556/13
See application file for complete search history.

(56) References Cited

U.S. PATENT DOCUMENTS

| | | | |
|---|---|---|---|
| 9,051,427 B2 | 6/2015 | Hasegawa et al. | |
| 2014/0171600 A1 | 6/2014 | Hasegawa et al. | |

FOREIGN PATENT DOCUMENTS

| | | |
|---|---|---|
| JP | 2004262909 A | 9/2004 |
| JP | 2009242385 A | 10/2009 |

(Continued)

OTHER PUBLICATIONS

JP 2010-278376, Dec. 9, 2010; English Translation from JPO provided.*

(Continued)

*Primary Examiner* — Venkataraman Balasubramanian
(74) *Attorney, Agent, or Firm* — Panitch Schwarze Belisario & Nadel LLP

(57) ABSTRACT

Provided are: a rare earth complex which has a novel structure, which exhibits compatibility with organic solvents and resins, and which exhibits excellent luminescent properties as a luminescent element; and a use thereof. This rare earth complex includes: a phosphine oxide compound represented by general formula (1); at least one rare earth ion selected from the group consisting of Ce, Pr, Nd, Pm, Sm, Eu, Gd, Tb, Dy, Ho, Er, Tm, Yb, and Lu; and a ligand compound. In the rare earth complex, the coordination numbers of the ligand compound and the phosphine oxide compound represented by general formula (1) to the rare earth ion are 8-10, and a plurality of the phosphine oxide compounds represented by general formula (1) and a plurality of the rare earth ions are provided with a crosslinked structure.

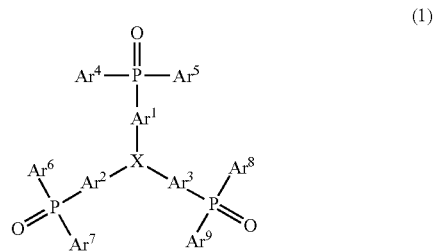

(1)

12 Claims, 10 Drawing Sheets

(51) Int. Cl.
    *C09D 11/00*    (2014.01)
    *C07F 9/58*     (2006.01)

(56) References Cited

FOREIGN PATENT DOCUMENTS

| JP | 2010095514 A  | 4/2010  |
|----|---------------|---------|
| JP | 2010278376 A  | 12/2010 |
| JP | 2011119591 A  | 6/2011  |
| JP | 2011157279 A  | 8/2011  |
| WO | 2012150712 A1 | 11/2012 |

OTHER PUBLICATIONS

JP 2011-157279, Aug. 18, 2011; English Translation from JPO provided.*
Electronegativity-Wikipedia downloaded Sep. 21, 2016.*
International Search Report dated Sep. 22, 2014 in International Application No. PCT/JP2014/067909.
International Preliminary Report on Patentability dated Aug. 18, 2015 in International Application No. PCT/JP2014/067909.
Miyata et al., "Thermostable Organo-phosphor: Low-Vibrational Coordination Polymers That Exhibit Different Intermolecular Interactions," ChemPlusChem, Vo. 77, pp. 277-280 (2012).

* cited by examiner

SHEET INTEGRATED RARE EARTH COMPLEX AND USE THEREOF

CROSS-REFERENCE TO RELATED APPLICATIONS

This application is a Section 371 of International Application No. PCT/JP2014/067909, filed Jul. 4, 2014, which was published in the Japanese language on Jan. 8, 2015, under International Publication No. WO 2015/002295 A1, and claims the benefit of priority to Japanese Patent Application No. 2013-141995, filed Jul. 5, 2013, the disclosures of both of which are incorporated herein by reference.

TECHNICAL FIELD

The present invention relates to a sheet integrated rare earth complex and use thereof.

BACKGROUND ART

Rare earth complexes have been continuously utilized as fluorescence and phosphorescence-emitting materials in the fields of electroluminescence and white LED illumination; the field of luminescent ink; the field of luminescent plastics; and the like. In each of these fields, rare earth complexes are expected to be compatible with organic solvents and resins.

Examples of rare earth complexes having compatibility with organic solvents and resins are given, for example, in Patent References 1 and 2 and in Nonpatent Reference 1. The complex described in Patent Reference 1 is linear tetraphosphine tetraoxide. The complex described in Patent Reference 2 is a complex that is formed as a crosslinked structure of multiple phosphine oxide multidentate ligands and a rare earth ion.

Patent Reference 1: Japanese Unexamined Patent Publication (KOKAI) No. 2010-95514

Patent Reference 2: WO2012/150712

Nonpatent Reference 1: K. Miyama, Y. Hasegawa et al., ChemPlusChem, 2012, 77, 277-280

Patent References 1 and 2 and Nonpatent Reference 1 are hereby incorporated in their entirety by reference.

SUMMARY OF THE INVENTION

Problem to be Solved by the Invention

The objects of the present invention are to provide a rare earth complex with a novel structure having compatibility with organic solvents and resins and having good light-emitting characteristics as a light-emitting material, and to provide applications of the same. In particular, the present invention provides a rare earth complex permitting the conservation of energy by light-emitting devices employing complexes, and affording highly efficient energy utilization from light absorption to light emission, and provides applications of the same.

Means of Solving the Problem

The present invention is as set forth below.

[1] A rare earth complex, comprising the phosphine oxide compound denoted by general formula (1):

[Chem. 1]

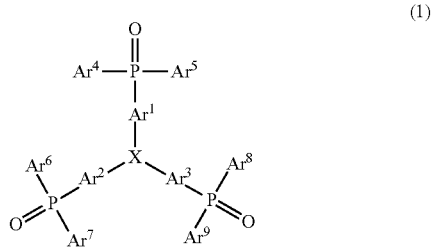

(in general formula (1), X denotes an atom having three-fold symmetry in a plan view of the structural formula containing the connectors of the atom, or a group of atoms having three-fold symmetry in a plan view of the chemical structural formula; and each of $Ar^1$ to $Ar^9$ independently denotes an aryl group which may comprise one or more substituents;

$Ar^4$ and $Ar^5$, $Ar^6$ and $Ar^7$, and $Ar^8$ and $Ar^9$, respectively, may form a phosphorus-containing hetero ring by binding);

one or more rare earth ions selected from the group consisting of Ce, Pr, Nd, Pm, Sm, Eu, Gd, Tb, Dy, Ho, Er, Tm, Yb and Lu; and a coordination compound;

wherein the coordination number of the coordination compound and the phosphine oxide compound denoted by general formula (1) relative to the rare earth ion being 8 to 10; and a plurality of the phosphine oxide compounds denoted by general formula (1) and a plurality of rare earth ions have a crosslinked structure.

[2] The complex according to [1], wherein the group of atoms is an aryl group which may comprise one or more substituents, or a heteroaryl group which may comprise one or more substituents.

[3] The complex according to [1] or [2], wherein each of Ar9 to Ar17 denotes a phenyl group which may comprise one or more substituents.

[4] The complex according to any one of [1] to [3], wherein the coordination compound is a multidentate compound.

[5] The complex according to [4], wherein the multidentate compound is a diketo compound.

[6] The complex according to [5], wherein the diketo compound is a compound denoted by general formula (2):

[Chem. 2]

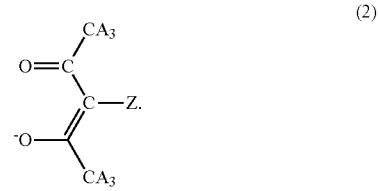

[7] The complex according to [5], wherein the diketo compound is at least one compound selected from the group consisting of acetyl acetone (acac), 2,2,6,6-tetramethylheptane-3,5-dione (TMHD), 1,1,1-trifluoroacetylacetone (TFA), and 1,1,1,5,5,5-hexafluoroacetylacetone (HFA).

[8] The complex according to any one of [1] to [7], wherein the phosphine oxide compound denoted by general formula (1) is at least one compound selected from the group consisting of (1-1) to (1-5) below:

[Chem. 3]

(1-1)

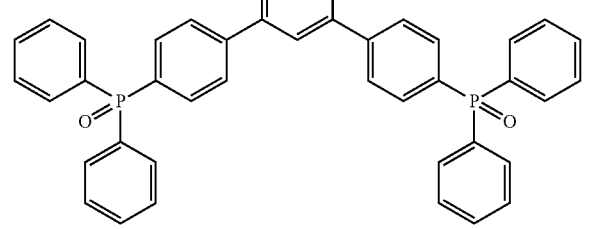

(1-2)

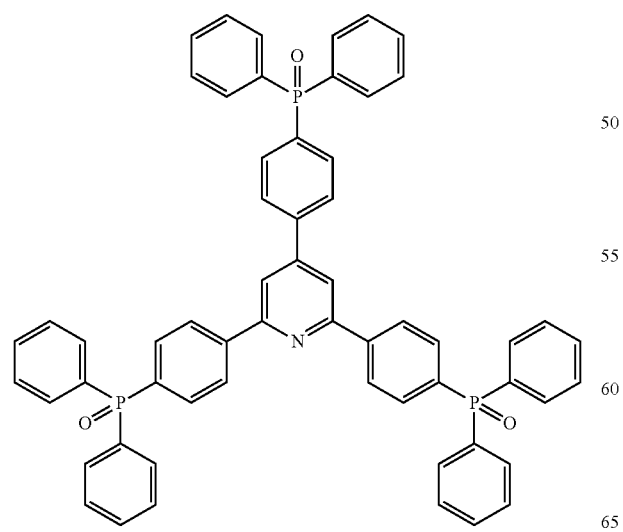

(1-3)

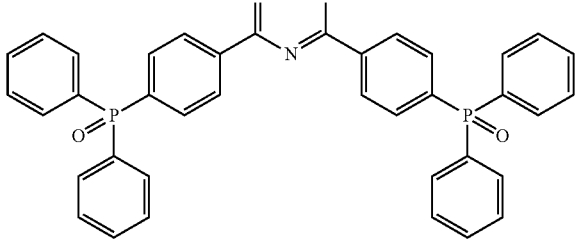

(1-4)

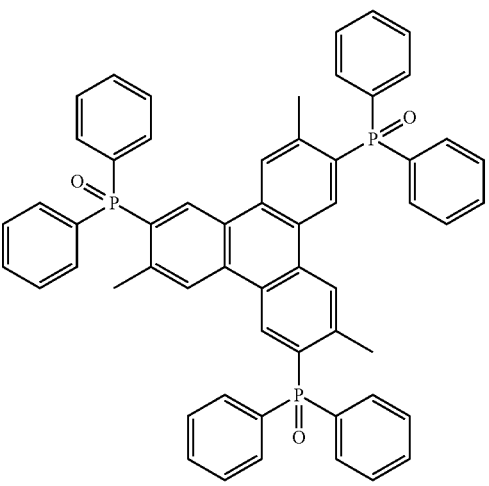

(1-5)

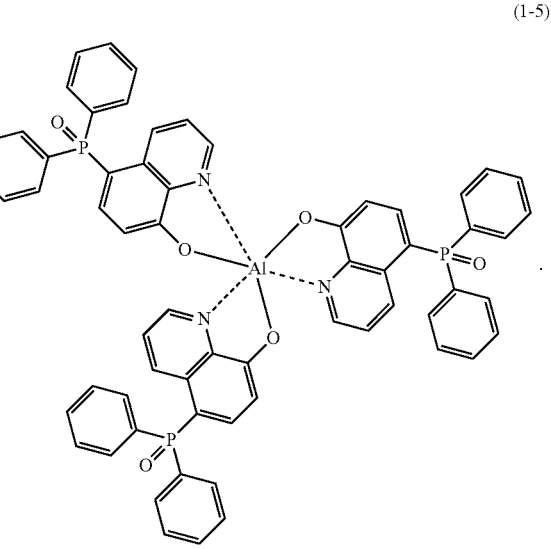

[9] The complex according to any one of [1] to [8], wherein the plurality of rare earth complexes having a crosslinked structure has an integrated sheet structure.

[10] The complex according to any one of [1] to [9], comprising an inter-ligand chain transfer (ILCT) band in the absorption spectrum thereof.

[11] The complex according to any one of [1] to [10], exhibiting triboluminescence.

[12] A light-emitting element employing the compound according to any one of [1] to [11] as a light-emitting material.

[13] A luminescent ink composition comprising the complex according to any one of [1] to [11].

[14] A luminescent plastic composition comprising the complex according to any one of [1] to [11].

Effect of the Invention

The present invention provides a rare earth complex having compatibility with organic solvents and plastics, affording good light-emitting characteristics, and in particular, exhibiting high-energy transfer efficiency. The present invention further provides a triboluminescent rare earth complex. Additionally, it provides applications for the rare earth complex of the present invention.

MODES OF CARRYING OUT THE INVENTION

[The Rare Earth Complex]

Figure 1:
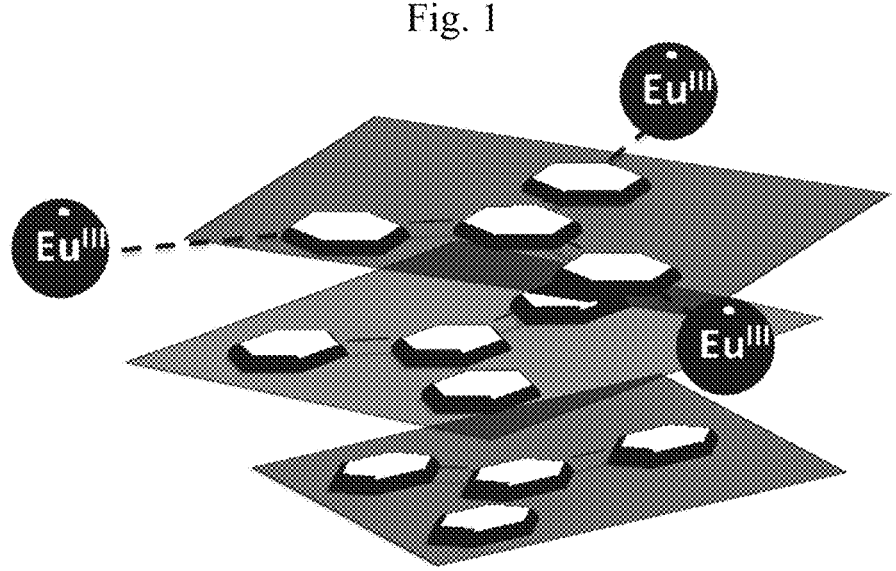
FIG. 1 is a schematic diagram of the integrated state of sheet-like rare earth complex molecules according to one embodiment of the invention.

The present invention relates to a rare earth complex comprising a phosphine oxide compound denoted by general formula (1), comprising one or more rare earth ions, and comprising coordination compounds, wherein the coordination number of the coordination compound and the phosphine oxide compound denoted by general formula (1) relative to the rare earth ions is 8 to 10, and a plurality of the phosphine oxide compounds denoted by general formula (1) and a plurality of rare earth ions have a crosslinked structure.

[Chem. 4]

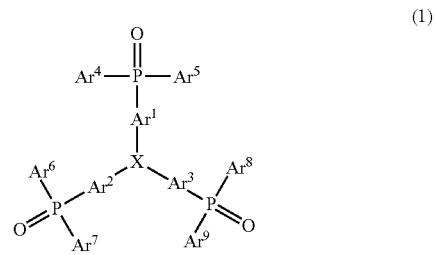

<The Phosphine Oxide Compound of General Formula (1)>

The phosphine oxide compound of general formula (1) is either a known compound or a compound that can be prepared by a known method.

In general formula (1), X denotes an atom having three-fold symmetry in a plan view of the structural formula containing the connectors of the atom, or a group of atoms having three-fold symmetry in a plan view of the chemical structural formula. Examples of atoms having three-fold symmetry in a plan view of the structural formula containing the connectors of the atom are aluminum, boron, germanium, and nitrogen (which contains an unshared electron pair but has C3 symmetry). Examples of groups of atoms having three-fold symmetry in a plan view of the chemical structural formula are an aryl group which may comprise one or more substituents and a heteroaryl group which may comprise one or more substitutents. The number of carbon atoms of the aryl group and heteroaryl group contained in the group of atoms is not specifically limited; 3 to 6 is desirable. The heteroaryl group contains hetero atoms selected from the group consisting of sulfur atoms, oxygen atoms, and nitrogen atoms. The number of hetero atoms varies suitably with the size of the heteroaryl group. For example, for a single ring, it will be 1 to 3, and for a fused ring (when two or more rings are present), it will be 1 to 3 per ring. From the perspective of having three-fold symmetry in a plan view of the chemical structural formula, specific examples of the group of atoms are phenyl groups and monocyclic six-membered heteroaryl groups. Examples of six-membered heteroaryl groups are pyridine rings, pyrmidine rings, and triazine rings.

Each of Ar$^1$ to Ar$^9$ independently denotes a hetero aryl group or an aryl group which may comprise one or more substituents. The hetero aryl group and the aryl group are the same as the hetero aryl group and the aryl group in the group of atoms of the examples of the X. Ar$^1$ to Ar$^9$ desirably denote phenyl groups which may comprise one or more substituents, and preferably denote phenyl groups.

A specific example of the phosphine oxide compound denoted by general formula (1) is at least one compound selected from the group consisting of (1-1) to (1-5) below:

(Chem. 5)

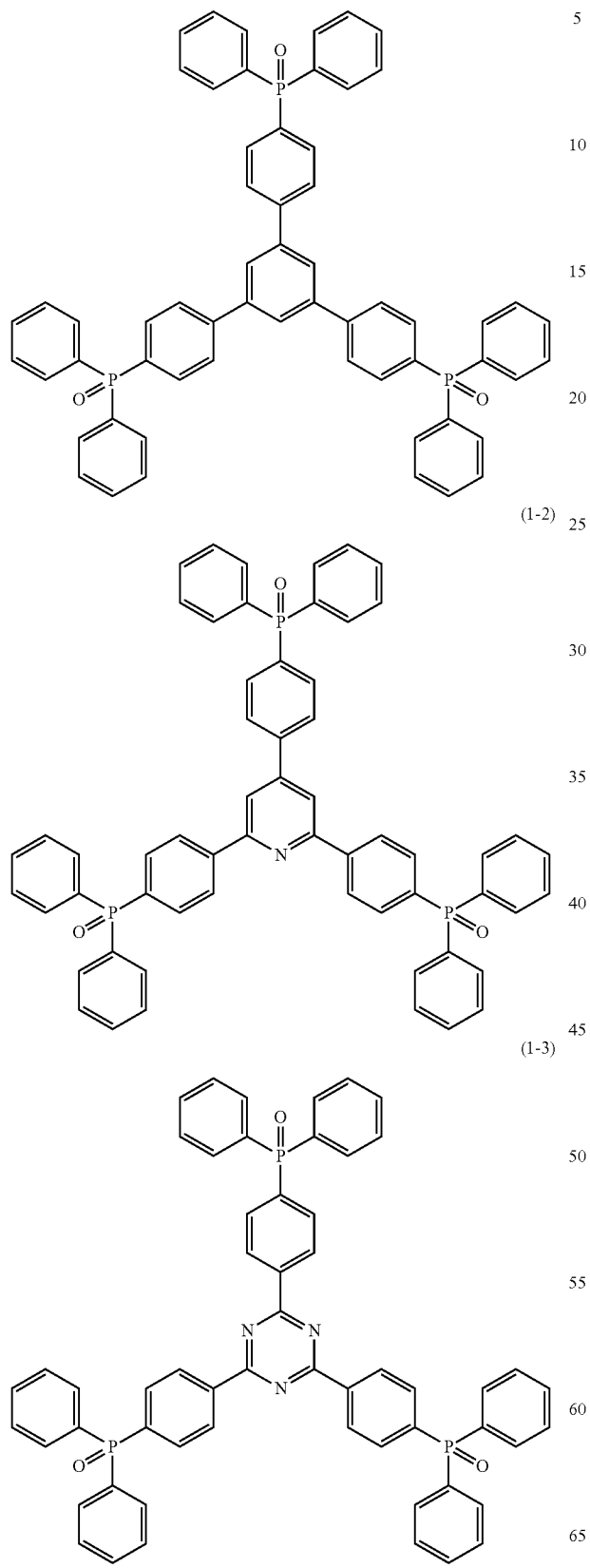

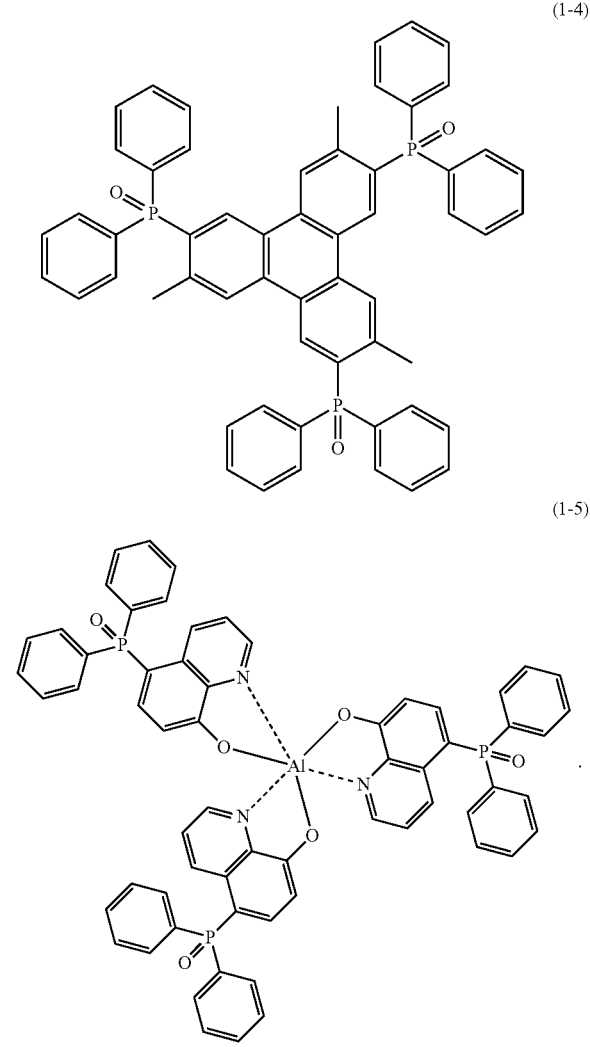

The phosphine oxide compound of general formula (1) is available in the form of commercial products. In addition, it can be synthesized by using oxidation of tertiary phosphine; reaction of phosphinyl chloride or phosphoryl dichloride with a Grignard reagent; coupling of a halogenated aryl and a diaryl phosphine oxide; hydrolysis of dihalophosphorane; or any other known method. Reference can be made to the following literature with regard to synthesizing the phosphine oxide compound of general formula (1):

[1] M. Stol, D. J. M. Snelders, H. Kooijman, A. L. Spek, G. P. M. Klink and G. Koten, *Dalton Trans.*, 2007, 2589-2593.

[2] I. O. Koshevoy, L. Koskinen, E. S. Smirnova, M. Haukka, T. A. Pakkanen, A. S. Melnikov, and S. P. Tunik, *Z. Anorg. Allg. Chem.* 2010, 636, 795-802.

The rare earth ion contained in the rare earth complex of the present invention consists of one or more rare earth ions selected from the group consisting of Ce, Pr, Nd, Pm, Sm, Eu, Gd, Tb, Dy, Ho, Er, Tm, Yb and Lu. These rare earth ions have 4f electrons. Thus, a coordination number of 8 to 10 can be achieved between the phosphine oxide compound denoted by general formula (1) and the rare earth ion of the coordination compound. La ions are commonly included among rare earth ions. However, La ions do not have 4f electrons and thus cannot achieve a coordination number of 8 to 10. The above rare earth ions are normally trivalent (3+). However, depending on the element, they can sometimes be divalent (2+) or tetravalent (4+).

The complex of the present invention comprises a coordination compound in addition to the phosphine oxide compound denoted by general formula (1). The coordination compound is desirably a multidentate coordination compound. Examples of multidentate coordination compounds are bidentate compounds, tridentate compounds, and tetradentate compounds. Among multidentate compounds, examples of bidentate compounds are diketo compounds. Examples of diketo compounds are the compounds denoted by general formula (2). In general formula (2), each instance of A independently denotes a hydrogen atom, an alkyl group with 1 to 6 carbon atoms, or a halogen atom. Z denotes a hydrogen atom or a deuterium atom. Examples of alkyl groups with 1 to 6 carbon atoms are methyl groups, ethyl groups, propyl groups (n- and iso-), butyl groups (n- and tert-), pentyl groups, and hexyl groups.

[Chem. 6]

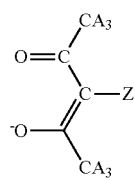

(2)

More specific examples of the diketo compound denoted by general formula (2) are one or more compounds selected from the group consisting of acetyl acetone (acac), 2,2,6,6-tetramethylheptane-3,5-dione (TMHD), 1,1,1-trifluoroacetylacetone (TFA), and 1,1,1,5,5,5-hexafluoroacetylacetone (HFA). These are known compounds.

Another example of a diketo compound is the facam derivative denoted by general formula (3). The facam derivative denoted by general formula (3) is a chiral compound. The rare earth complex of the present invention in which the facam derivative denoted by general formula (3) is coordinated with a rare earth ion will exhibit circularly polarized luminescence characteristics.

[Chem. 7]

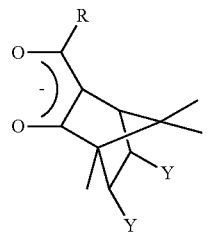

(3)

In general formula (3), each instance of Y—the two instances of which may be identical or different—denotes a hydrogen atom, deuterium atom, halogen atom, hydrocarbon group with 1 to 20 carbon atoms, hydroxyl group, nitro group, amino group, sulfonyl group, cyano group, silyl group, phosphonic acid group, diazo group, or mercapto group. R denotes an optionally substituted hydrocarbon group with 1 to 20 carbon atoms, hydroxyl group, nitro group, amino group, sulfonyl group, cyano group, silyl group, phosphonic acid group, diazo group, or mercapto group. Examples of optional substituents present on the hydrocarbon group with 1 to 20 carbon atoms are halogen atoms (F, Cl, Br, and I). The hydrocarbon group with 1 to 20 carbon atoms is desirably an alkyl group with 1 to 6 carbon atoms. More specific examples are methyl groups, ethyl groups, propyl groups (n- and iso-), butyl groups (n- and Pert-), pentyl group, and hexyl groups. An example of a facam derivative is D-facam in which both instances of Y denote hydrogen atoms and R denotes a trifluoromethyl group.

In the complex of the present invention, the coordination number of the coordination compound and phosphine oxide compound denoted by general formula (1) relative to the rare earth ion is eight to ten-coordination. The rare earth ions contained in the complex of the present invention have 4f electrons. It is conceivable that the coordination structure is formed by 4f-5d interaction. Thus, the coordination number of ligands relative to the rare earth ions is 8 to 10. Which coordination number is exhibited from 8 to 10 is determined by the ligands employed, specifically the type of coordination compound in addition to the phosphine oxide compound denoted by general formula (1). When the above diketo compound serves as a coordination compound, eight-coordination is exhibited. The further addition of organic molecules containing hetero elements such as pyridine yields nine-coordination or ten-coordination. Whether the structure is a nine-coordination or ten-coordination structure is determined by the coordination force of the organic molecule added and the size of the molecule.

(Reference document: Y. Hasegawa, et al., J. Phys. Chem. A 2008, 112, 803-807)

In the rare earth complex of the present invention, a plurality of the phosphine oxide compound denotes by general formula (1) and a plurality of rare earth ions have a crosslinked structure. The case where the phosphine oxide compound of general formula (1) is compound (1-1) above, the coordination compound is 1,1,1,5,5,5-hexafluoroacetylacetone (HFA), and the rare earth ion is $Eu^{3+}$; and the case where the phosphine oxide compound of general formula (1) is compound (1-3) above, the coordination compound is 1,1,1,5,5,5-hexafluoroacetylacetone (HFA), and the rare earth ion is $Eu^{3+}$ will be given as examples below. The phosphine oxide compound of general formula (1) comprises three phosphine oxide groups, each of which is coordination bonded to the rare earth ion. One of the phosphine oxide groups of each of the two phosphine oxide compounds of general formula (1) is coordination bonded to a single rare earth ion. In addition to the two phosphine oxide groups, three HFA molecules are coordination bonded to a single rare earth ion. In the case of this complex, there is eight-coordination.

The three phosphine oxide groups of the phosphine oxide compound of general formula (1) are approximately equivalent. Each bonds to a different rare earth ion. Overall, there is a crosslinked structure that spreads out in planar fashion. The repetition number n in the crosslinked structure, for example, falls within a range of 2 to 10,000. The molecular weight of the rare earth complex, for example, falls within a range of 1,000 to 1,000,000.

[Chem. 8]

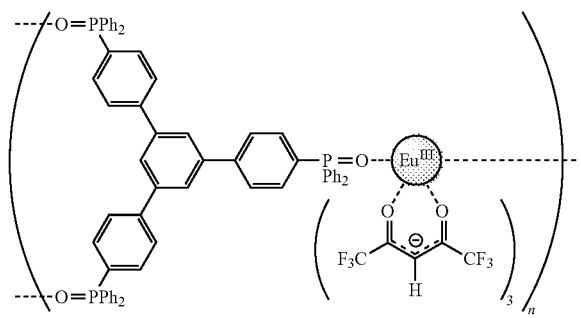

[Chem. 9]

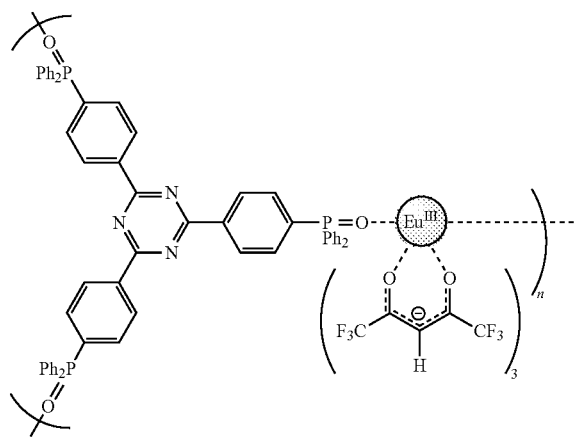

Eu-TPPTZ

The rare earth complex of the present invention can be synthesized by mixing the phosphine oxide compound denoted by general formula (1) and a coordination compound and rare earth ion-containing compound in a solvent. The mixing ratio of the phosphine oxide compound denoted by general formula (1) and the coordination compound and rare earth ion-containing compound can be suitably determined based on the complex being targeted. For example, the coordination compound and rare earth ion-containing compound can be mixed in a range of 0.1 to 5 equivalents, desirably in a range of 0.5 to 3 equivalents, and preferably within a range of 0.8 to 1.2 equivalents, per equivalent of the phosphine oxide compound denoted by general formula (1). The solvent employed need only be one in which the phosphine oxide compound denoted by general formula (1), and the coordination compound and rare earth ion or rare earth ion-containing compound will dissolve. For example, methanol, ethanol, acetone, toluene, chloroform, dichloromethane, dichloroethane, pyridine, DMSO, and DMF can be employed. The coordination compound and rare earth ion-containing compound can be a rare earth ion complex compound comprising a coordination compound as at least a portion of the ligands. A rare earth ion complex compound in which the coordination compound is present as a portion of the ligands and the remaining ligands are ligands having a weaker coordination force on rare earth ions than the phosphine oxide compound denoted by general formula (1) is desirable from the perspective of facilitating synthesis of the rare earth complex of the present invention. Examples of ligands having a weaker coordination force on rare earth ions than the phosphine oxide compound denoted by general formula (1) are water ($H_2O$), methanol, and ethanol.

In the examples given farther below, as indicated by the following reaction equation, coordination compound (1-1) or (1-3) and a rare earth-containing compound in the form of $Eu(hfa)_3(H_2O)_2$ were employed to conduct a reaction in methanol solvent. The reaction temperature and duration were not specifically limited. The reaction temperature, for example, can be a temperature falling within a range of from ordinary temperature (such as 20° C.) to the boiling point of the solvent. The reaction duration can be suitably selected taking into account the production rate and the like of the complex of the present invention being targeted. For example, it can fall within a range of 1 to 12 hours. However, no limitation to this range is intended; this is merely given by way of example.

[Chem. 10]

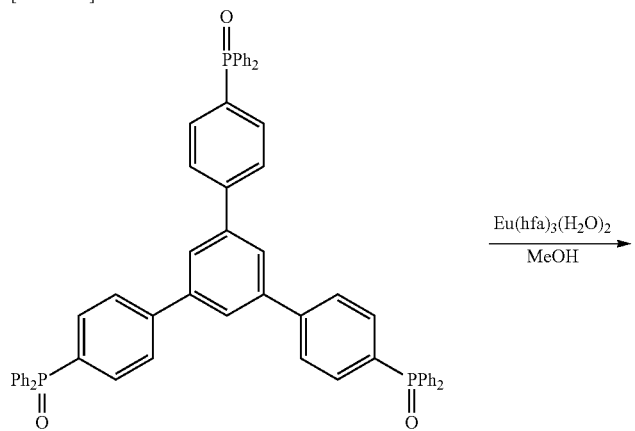

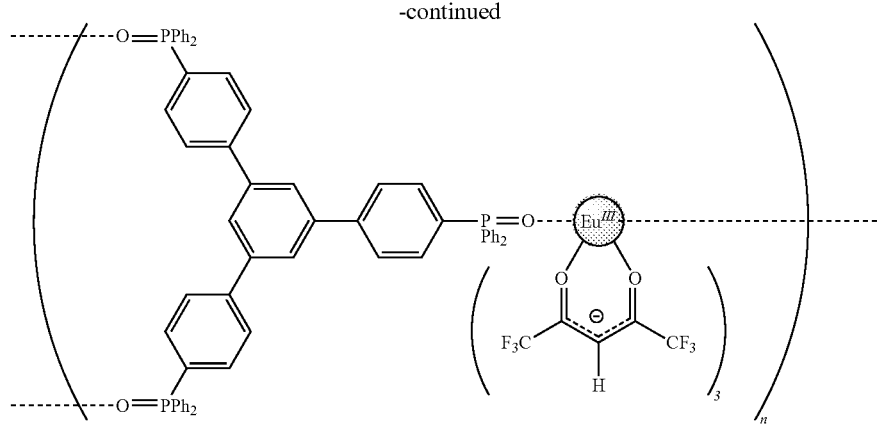

[Chem. 11]

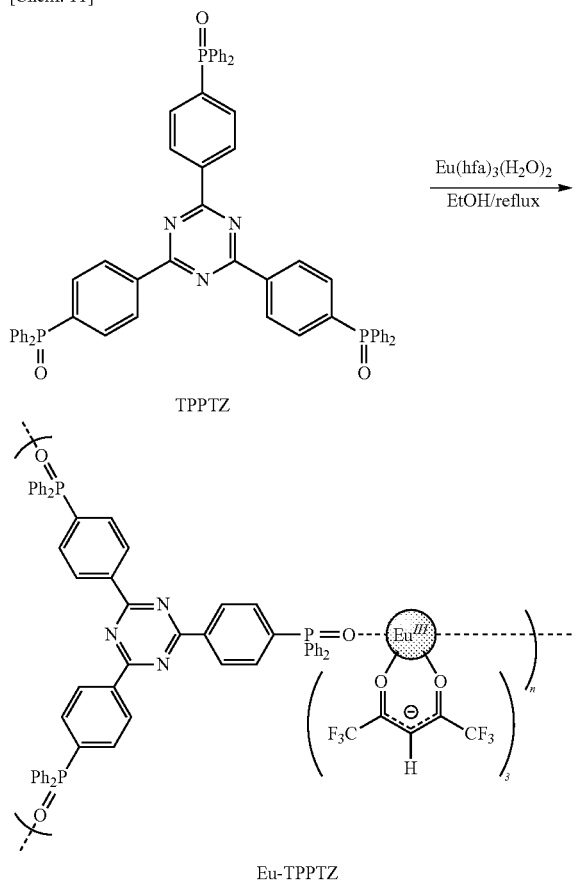

Since a single molecule of the rare earth complex of the present invention spreads out in planar fashion overall, when multiple molecules of the rare earth complex are crosslinked, they become a polymer and can become a material with a sheet-like crosslinked structure. Multiple sheet-like rare earth complex molecules can be present, and multiple sheet-like rare earth complex molecules can integrate to constitute a block of rare earth complex. A schematic diagram of the integrated state of sheet-like rare earth complex molecules is shown in FIG. 1. In this schematic diagram, only the Eu ions of the complex molecule of the uppermost layer are shown; the Eu ions of the second and third layers of the complex molecules have been omitted. Each sheet-like rare earth complex molecule produces weak stacking due to hydrogen bonds. The ligands comprised of the phosphine oxide compound denoted by general formula (1) produce distortion in the structure. As a result, it is presumed that spatial groups end up containing asymmetric centers. As a result, as set forth farther below, the absorption band of the rare earth complex of the present invention exhibits an absorption band that is attributed to inter-ligand charge transfer (referred to as an ILCT band hereinafter in the present specification), and strong triboluminescence.

An ILCT band is present in the absorption spectrum of the rare earth complex of the present invention. As a result, it exhibits high-energy transfer efficiency and high light-emission strength. The ILCT band is a new absorption band caused by a solid state appearing on the long wavelength side of the absorption band due to a $\pi$-$\pi^*$ transition.

Further, the rare earth complex of the present invention exhibits triboluminescence. The term triboluminescence is a unique light-emission phenomenon that appears in the course of pulverizing a bulk solid by means of mechanical stress. It was first observed about 400 years ago by Francis Bacon in the form of light being emitted by crushing sugar crystals. There is broad debate about the principles behind triboluminescence. Generally, when noncentrosymmetric bulk crystals are pulverized, the cracks undergo electrostatic polarization, charging and discharging. This is thought to excite the crystals and emit light. Various materials exhibiting triboluminescence have been reported to date, such as organic crystals, polymers, and metal complexes.

Much research has been conducted on the triboluminescence of Eu(III) complexes. In the case of Eu(III) complexes, Eu(III) ions are excited to cause fluorescence by the current that flows in the course of pulverizing the crystals, resulting in the observation of a strong red triboluminescence derived from Eu(III) ions. Light energy is removed by light excitation in common Eu(III) complexes. In systems where electrical energy is converted to light energy by friction, various applications can be anticipated. In the rare earth complex of the present invention, the Eu(III) complex exhibiting the strong emission of red light of high chromatic purity exhibits triboluminescence. Thus, application to the field of stress light emission, such as to pressure sensors, can be anticipated.

<Light-Emitting Elements>

The present invention covers light-emitting elements employing the complex of the present invention as a light-emitting material. The light-emitting element of the present invention can comprise a thin film of the complex of the present invention. More specifically, the rare earth complex of the present invention can be employed, for example, in the light-emitting layer (light-emitting medium) of a white LED element and in the light-emitting layer of an organic electroluminescent element. The light-emitting element of the present invention can also be used in display and illumination. The rare earth complex of the present invention can also be used, for example, in fluorescent ink compositions, in luminescent security ink compositions, and in other luminescent ink compositions. Still further, development of various applications of the rare earth complex of the present invention in which a chiral diketo compound is employed as a portion of the ligands can be anticipated, such as security sensors employing circularly polarized luminescence, labeling agents (immunoassays) for uses relating to biology, and circularly polarized light sources (for example, see WO2008/111293). Additionally, the rare earth complex of the present invention can be employed, for example, as the light-emitting thin films for enhancing light-energy conversion efficiency that are mounted on the surface of silicon solar cells (for example, see Japanese Unexamined Patent Publication (KOKAI) Heisei No. 9-230396). Additionally, the rare earth complex of the present invention containing two or more rare earth ions can be employed in temperature sensors (see K. Miyata, Y. Konno, T. Nakanishi, A. Kobayashi, M. Kato, K. Fushimi, Y. Hasegawa, Angew. Chem. Int. Ed. 52, 6413-6416 (2013)).

When employing the rare earth complex in these applications, a single type of the rare earth complex can be employed, or two or more types can be combined for use.

The rare earth complex can be employed in mixtures where it is incorporated as an essential component and other ions, compounds, and the like are additionally incorporated. It suffices for the rare earth complex to be incorporated into such mixtures; to the extent that the effect of the present invention is not compromised, rare earth metal ions, rare earth complexes not coordinated with the compound of the present invention, and the like can be further incorporated.

(1) The White LED Element

The same configurations as in known LED elements can be adopted in the white LED element of the present invention, with the exception that the above rare earth complex is incorporated into the light-emitting medium (fluorescent material) constituting the light-emitting layer. Examples are LED elements having light-emitting layers comprised of LED chips and light-emitting media.

In LED chips, electric energy is received by an electrode, and light is generated and released. A light-emitting medium (fluorescent material) that absorbs light emitted by an LED chip releases light of a different wavelength from the light absorbed. At that time, by combining the light that is released by the LED chip with light released by a fluorescent material, it is possible to create a new color of light. In the present invention, it is possible to emit white light by incorporating the above rare earth complex into a fluorescent material. The rare earth complex can be suitably dissolved in an organic medium. Since it will essentially not precipitate out of an organic medium, white light can be released with high efficiency (at a high light extraction efficiency).

It suffices for the LED chip to be an element that releases light in the ultraviolet to near ultraviolet to visible to near infrared region; there is no specific limitation. Examples are blue LEDs and near ultraviolet LEDs.

The light-emitting medium is obtained by dissolving the rare earth complex in an organic medium. In the present invention, it is possible to control the color emitted by the light-emitting medium by suitably selecting the rare earth element ions (central element ions) in the rare earth complex. For example, in a light-emitting medium containing a rare earth complex in which all of the central element ions are $Eu^{3+}$, red light can be emitted. Further, a light-emitting medium containing a rare earth complex in which all of the central element ions are $Tb^{3+}$ will emit green light. Still further, a light-emitting medium containing a rare earth complex in which the central element ions are rare earth element ions other than $Eu^{3+}$ and $Tb^{3+}$ (for example, where all of the central element ions are $Tm^{3+}$) will emit blue light.

Two or more of the rare earth complexes set forth above can be incorporated into the light-emitting medium. From the perspective of lowering the light extraction efficiency and the like, it is better not to incorporate particles of known fluorescent inorganic compounds into the light-emitting medium. However, to the extent that the effect of the present invention is not impeded, these particles can be incorporated as needed.

Examples of the above particles are yellow light-emitting inorganic compound particles that function by activating $Y_3Al_5O_{12}$ (YAG) with Ce; blue light-emitting inorganic compound particles such as particles that function by activating $Sr_{10}(PO_4)_6Cl_2$ with Eu, particles that function by activating $Ca_{10}(PO_4)_6C_{12}$ with Eu, particles that function by activating $Ba_{10}(PO_4)_6C_{12}$ with Eu, particles that function by activating $BaMgAl_{10}O_{17}$ with Eu, and particles that function by activating $Ba_3MgSi_2O_8$ with Eu; inorganic compound particles emitting green light such as particles that function by activating $SrGa_2S_4$ with Eu, particles that function by activating $CaAl_2O_4$ with Eu, particles that function by activating $BaAl_2O_4$ with Eu, and particles that function by activating $SrAl_2O_4$ with Eu; and inorganic compound particles that emit red light such as particles that function by activating SrS with Eu, particles that function by activating CaS with Eu, particles that function by activating $CaAlSiN_3$ with Eu, and particles that function by activating $Ba_3MgSi_2O_8$ with Eu or Mn. These particles can be employed singly, or in combinations of two or more.

For example, when the following LED chips are combined with a light-emitting medium, suitable white light can be obtained:

(1) LED chip: Blue LED (such as InGaN); light-emitting medium: red light-emitting rare earth complex+yellow light-emitting inorganic compound particle (such as particles that function by activating $Y_3Al_5O_{12}$ (YAG) crystals with Ce)

(2) LED chip: Blue LED (such as InGaN); light-emitting medium: red light-emitting rare earth complex+green light-emitting rare earth complex (3) LED chip: near ultraviolet LED (such as InGaN); light-emitting medium: blue light-emitting inorganic compound particle (such as particles that function by activating $Sr_{10}(PO_4)_6Cl_2$ with Eu, particles that function by activating $Ca_{10}(PO_4)_6Cl_2$ with Eu, and particles that function by activating $Ba_{10}(PO_4)_6Cl_2$) with Eu+red light-emitting rare earth complex+green light-emitting rare earth complex (4) LED chip: near ultraviolet LED (such as InGaN); light-emitting medium: red light-emitting rare earth complex+green light-emitting rare earth complex+blue light-emitting rare earth complex Examples of the above organic media are organic solvents and liquid polymers.

Examples of the above organic solvents are fluorine-based solvents. These organic solvents can be employed singly or as mixtures comprised of two or more solvents.

Examples of the liquid polymer are fluororesins and silicone resins. The fluororesins and silicone resins can be employed in the form of suitable commercial products. Examples of commercial products of fluororesins are Teflon (registered trademark) AF (made by Dupont) and Cytop (made by Asahi Glass). Examples of commercial products of silicone resins are polydimethyl siloxane, polymethylphenyl siloxane, and polydiphenyl siloxane.

In particular, liquid polymers are desirable and fluororesins are preferred as organic media. Fluororesins have characteristics such as a high glass transition point, high moisture resistance, and low gas permeability. Thus, the use of a fluororesin as the organic medium enhances the light-emitting characteristics, emission lifetime, durability, and the like of light-emitting medium 3.

The content of the rare earth complex in the light-emitting medium is not specifically limited; about 5 to 90 mass % is desirable.

The content of the fluorescent inorganic compound particles in the light-emitting medium is not specifically limited so long as it does not impede the present invention.

The white LED element of the present invention can be used in various LEDs such as bullet-type LEDs and surface-mounted LEDs. The same configuration as that of known LEDs can be adopted as the specific configuration of the LED with the exception that the above white LED element is utilized.

(2) Organic Electroluminescent (EL) Element

The organic EL element of the present invention comprises a light-emitting layer comprising the above mentioned rare earth complex.

Organic electroluminescent elements normally have a configuration comprised of, sequentially layered on a substrate, an anode, a charge (hole) transport layer, the light-emitting layer, a charge (electron) transport layer, and a cathode. The content of the rare earth complex in the light-emitting layer can be, for example, about 5 to 100 mass %.

The light-emitting layer can be formed solely of the rare earth complex of the present invention, or can contain other compounds in addition to the rare earth complex of the present invention. For example, it can contain the charge (hole) transport layer material or the charge (electron) transport layer material described below as a host compound.

The thickness of the light-emitting layer must be at least adequate to prevent the formation of pinholes. Excessive thickness is undesirable in that the resistance of the element increases and a high drive voltage becomes necessary. Accordingly, the thickness of the light-emitting layer is about 0.0005 to 10 μm, desirably about 0.001 to 1 μm, and preferably, about 0.005 to 0.2 μm.

The method of forming the light-emitting layer is not specifically limited. Examples are the method of vapor depositing the rare earth complex on the hole transport layer, or methods of coating the luminescent ink composition described farther below such as the spin coating method or printing methods such as the ink jet method.

It suffices for the substrate to be transparent. Examples are glass, quartz, and optically transparent plastic films (polyethylene terephthalate (PET), polyethylene naphthalate (PEN), polyether sulfone (PES), polyetherimide, polycarbonate (PC), and the like). The thickness of the substrate is not specifically limited so long as it does not impede the effect of the present invention.

By way of example, indium tin oxide (ITO), which is an electrically conductive material with a high work function, can be employed as the anode material. The thickness of the anode can be about 0.1 to 0.3 μm.

By way of example, an arylamine compound such as triarylamine can be employed as the material of the charge (hole) transport layer. One such material, or a combination of two or more such materials, can be employed.

By way of example, tris(8-hydroxyquinolinol)aluminum, triazoles, phenanthrolines, and oxadiazoles can be employed as the materials of the charge (electron) transport layer. One such material, or a combination of two or more such materials, can be employed.

The thickness of each of these charge transport layers is normally about 0.0005 μm to 10 μm, desirably about 0.001 to 1 μm.

A metal with a low work function such as aluminum, magnesium, indium, aluminum-lithium alloy, or magnesium-silver alloy can be used as the cathode material. The thickness of the cathode is desirably about 0.01 to 0.5 μm.

The anode, hole transport layer, electron transport layer, and cathode can be formed by known methods such as resistance heating vapor deposition, vacuum vapor deposition, or sputtering employing the various above materials.

The organic EL element of the present invention can be employed as an illuminator such as the backlight of a color liquid-crystal display device, as a display, or the like.

(3) The Luminescent Ink Composition

The luminescent ink composition of the present invention contains the above rare earth complex. The light emitted by the rare earth complex in natural lighting is essentially colorless. The luminescent ink composition of the present invention can be used as a fluorescent ink and as a luminescent security ink.

When the rare earth complex is irradiated with ultraviolet light, the complex emits colored light, making it possible to observe the light emitted. Accordingly, an ink composition in which the rare earth complex has been dissolved can be printed on various substrates to permit viewing of the printed contents only when irradiated with ultraviolet light employing a black light or the like. For example, the ink composition can be printed on substrates such as paper bills, documents, publications, and cards to impart a security function of preventing forgery, unauthorized copying, and the like.

The color of the light emitted varies with the type of the central element ion of the rare earth complex. For example, when the central element ion is $Eu^{3+}$, the complex will emit an intensely red light. When the central element ion is $Tb^{3+}$, the complex will emit intense green light. When multiple central element ions are present in the rare earth complex, the multiple rare earth element ions are desirably all identical.

Two or more types of rare earth complex compositions can be incorporated into the above ink composition.

For example, it is possible to prepare a two-color mixture-type ink by mixing a first fluorescent material in the form of the rare earth complex of the present invention comprised of a central element ion in the form of $Tb^{3+}$ that emits intense green light when irradiated with a black light lamp emitting ultraviolet radiation in wavelengths of 365 nm and 254 nm and a second fluorescent material in the form of the rare earth complex of the present invention comprised of a central element ion in the form of $Eu^{3+}$ that emits almost no red light when irradiated with a black light-emitting ultraviolet radiation with a wavelength of 254 nm but emits intense red light when irradiated with a black light lamp emitting ultraviolet radiation with a wavelength of 365 nm.

When the above ink composition is irradiated with a black light lamp emitting ultraviolet radiation with a wavelength of 365 nm, the first and second fluorescent materials emit a color close to yellow by emitting a mixture of green and red. When irradiated with a black light lamp emitting ultraviolet radiation with a wavelength of 254 nm, the second fluorescent material emits almost no light, so just the green of the first fluorescent material is emitted.

Since differing hues can be distinguished using the two wavelength regions in this manner, it is easier to distinguish between forgeries and authentic items.

The content of the rare earth complex in the fluorescent ink composition of the present invention can be suitably set based on the type of substrate or the like. A content of about 0.001 to 30 mass % is desirable, and about 0.05 to 3 mass % is preferred.

Additives such as solvents, resins (binders), penetrating agents, defoamers, dispersing agents, and colorants can be incorporated as needed into the fluorescent ink composition of the present invention. In particular, in the ink composition of the present invention, the rare earth complex is desirably dissolved in a solvent.

The above solvents capable of dissolving the rare earth complex can be employed as this solvent. Examples are ketone solvents such as acetone, methyl ethyl ketone, and cyclohexanone; aliphatic hydrocarbon solvents such as n-hexane, cyclohexane, n-pentane, and n-heptane; aromatic hydrocarbon solvents such as toluene and xylene; ether solvents such as tetrahydrofuran, 1,4-dioxane, methyl cellosolve, ethyl cellosolve, butyl cellosolve, diethylene glycol monobutyl ether, and ethylene glycol monobutyl ether; alcohol solvents such as methanol, ethanol, propanol, isopropanol, ethylene glycol, diethylene glycol, propylene glycol, and glycerol; ester solvents such as ethyl acetate and butyl acetate; and 2-pyrrolidone; N-methyl-2-pyrrolidone. These solvents can be suitably selected based on the application or the like of the fluorescent ink composition, and employed singly or as mixtures of two or more solvents.

The above resin (binder) is desirably one that can fix the rare earth complex well to the substrate and will dissolve well in the above solvent. The resin can be optically transparent or opaque. Examples are polyvinyl resins, phenol resins, amino resins, polyamide resins, nylon resins, polyolefin resins, acrylic resins, epoxy resins, urethane resins, cellulose resins, polyester resins, silicone resins, and fluorine-based resins. These resins can be suitably selected based on the application or the like of the fluorescent ink composition, and can be employed singly or in combinations of two or more.

The penetrating agent is added with the goal of accelerating penetration of the ink composition into paper or the like and accelerating the apparent drying property. Examples of penetrating agents are glycol ether, alkylene glycol, sodium lauryl sulfate, sodium oleate, sodium dodecylbenzene sulfonate, and sodium dioctyl sulfosuccinate. These penetrating agents can be employed singly or in combinations of two or more.

The defoaming agent is added with the goal of preventing the generation of bubbles during movement and during manufacturing of the ink composition. An anionic, nonionic, cationic, or amphoteric surfactant can be employed as the defoaming agent. Examples of anionic surfactants are fatty acid salts, alkyl sulfates, alkyl phosphates, and alkyl ether phosphates. Examples of nonionic surfactants are polyoxyethylene alkyl ethers, polyoxyethylene alkylaryl ethers, polyoxyethylene oxypropylene block copolymers, sorbitan fatty acid esters, glycerol fatty acid esters, polyoxyethylene fatty acid esters, polyoxyethylene alkyl amines, and fluorine-based and silicone-based compounds. Examples of cationic surfactants are quaternary ammonium salts and alkyl pyridinium salts. Examples of amphoteric surfactants are alkyl betaine, alkyl amine oxides, and phosphatidyl choline. These surfactants can be employed singly or in combinations of two or more.

Examples of the above dispersing agent are surfactants such as stearic acid soap, oleic acid soap, rosin acid soap, Na-di-β-naphthylmethane disulfate, sodium lauryl sulfate, sodium diethylhexyl sulfosuccinate, and sodium dioctyl sulfosuccinate. These surfactants can be employed singly or in combinations of two or more.

A known pigment or dye can be employed as the colorant. Examples are organic dyes and pigments such as azos, azomethines, quinacridones, anthraquinones, dioxazines, quinolines, perylenes, isoindolinones, and quinoophthalones. These colorants can be employed singly or in combinations of two or more.

The content of the various above additives in the fluorescent ink composition of the present invention is not specifically limited and can be suitably set based on the type of substrate, application, and the like. The content of the resin (binder) in the fluorescent ink composition of the present invention is desirably 0.5 to 30 mass %, preferably 1 to 10 mass %. When the content of the resin is less than 0.5 mass %, the rare earth complex cannot be suitably fixed to an impermeable substrate. When the content of the resin exceeds 30 mass %, the area around the rare earth complex in the fluorescent ink composition is thickly covered by resin (binder), running the risk of decreased light emission by the rare earth complex.

<Rare Earth Complex-Containing Plastic>

The present invention covers a luminescent plastic composition containing the rare earth complex of the present invention. The plastic material that is employed in the luminescent plastic composition is not specifically limited. Various materials can be utilized. Examples of plastic materials are polyethylene resins, polypropylene resins, polyvinyl chloride resins, urea resins, fluororesins, polyester resins, polyamide resins, polyacetal resins, polycarbonate resins, polyarylate resins, polysulfone resins, polyphenylene sulfide resins, polyether sulfone resins, polyallylsulfone resins, polytetrafluoroethylene resins, phenol resins, unsaturated polyester resins, epoxy resins, polyimide resins, and polyamide-imide resins. The method of blending the rare earth complex and molding is not specifically limited. Examples are injection molding, blow molding, compression molding, extrusion molding, reaction molding, hollow molding, heat molding, and FRP molding.

The luminescent plastic composition of the present invention can be used, for example, as a luminescent thin film mounted on the surface of a silicon solar panel to enhance the light-energy conversion efficiency (for example, Japanese Unexamined Patent Publication (KOKAI) Heisei No. 9-230396).

EXAMPLES

The present invention is described in greater detail below through examples. However, there is no intent to limit the present invention to the examples.

Sheet integrated-type Eu(III) complex [Eu(hfa)$_3$(tppb)]$_n$ was synthesized according to the following scheme. Commercial products (Kanto Chemical, Tokyo Chemical Industry, Wako Pure Chemical Industries) were employed as the starting materials, catalysts, and solvents. Identification of compounds was made by $^1$H-NMR, EI-Mass Spectra, ESI-Mass Spectra, FAB-Mass Spectra, FT-IR measurement, and elemental analysis.

[Chem. 13]
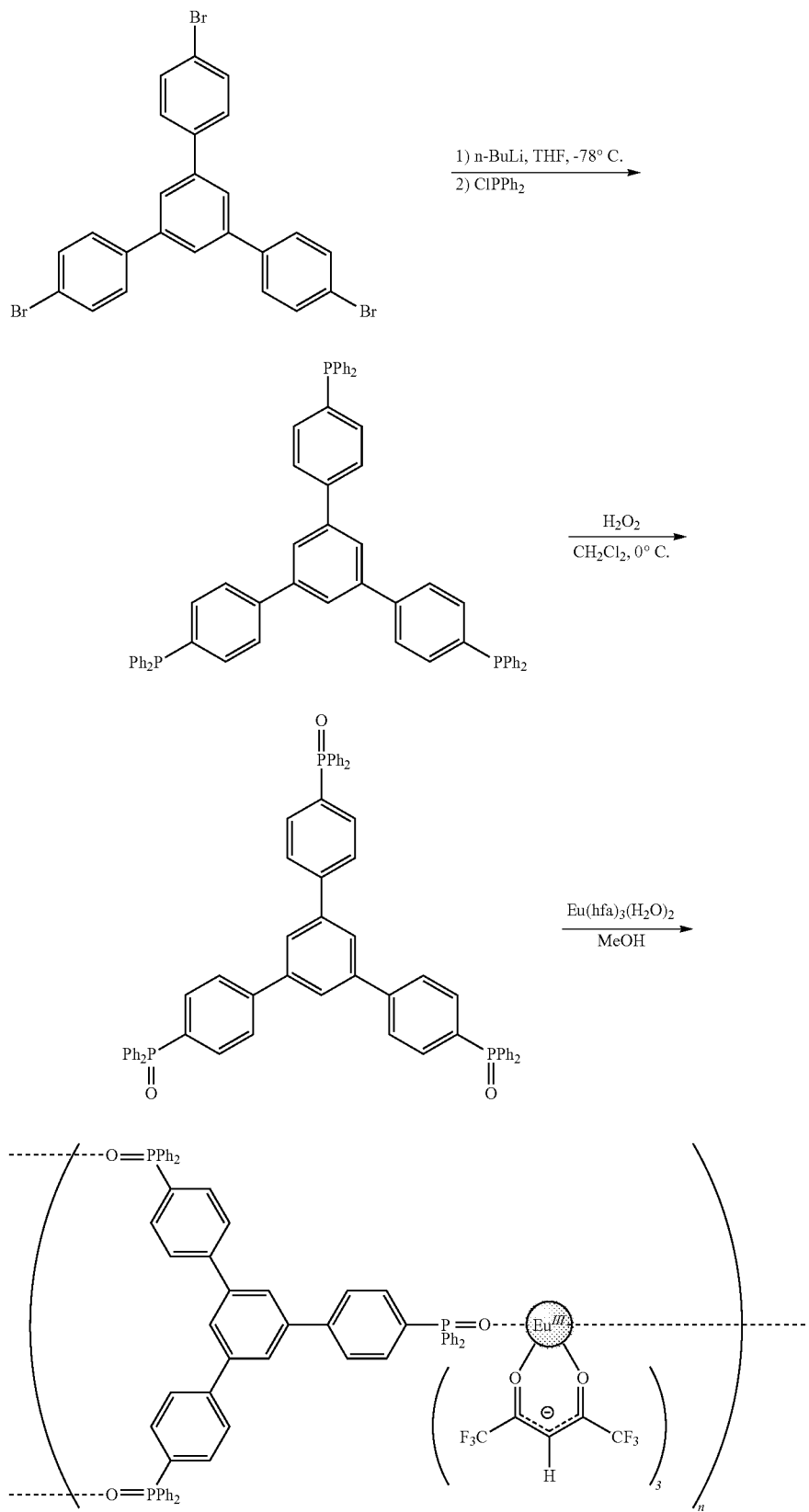

Reference Example 1: Ligand Synthesis

Tridentate ligand tppb was synthesized according to the reported literature. Synthesis of 1,3,5-Tris(4-diphenylphosphorylphenyl)benzene (tppb)[1][2]

[Chem. 14]

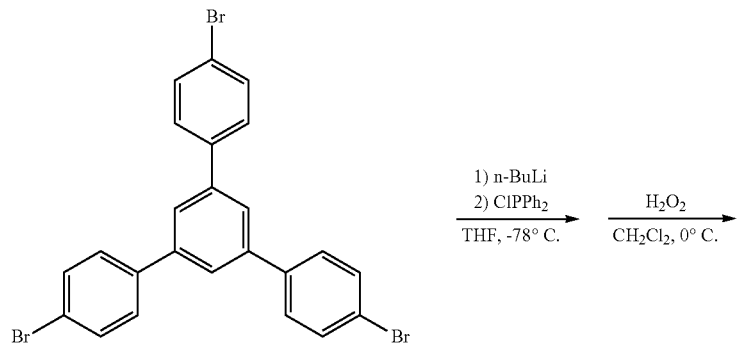

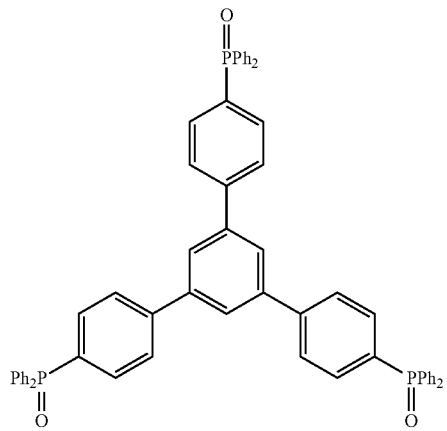

A 300 mL capacity three-necked flask was flame dried and backfilled with Ar. A 1.55 g (2.86 mmol) quantity of 1,3,5-tris(4-bromophenyl)benzene and 200 mL of THF were added and the mixture was cooled to −78° C. with liquid nitrogen/MeOH. A 7 mL (11.2 mmol) quantity of n-BuLi was then added and the mixture was stirred for 2 hours at −78° C. To the cloudy, yellowish-white solution was added 2.03 mL (11.3 mmol) of ClPPh$_2$ in dropwise fashion. The transparent yellow solution was stirred for 1 hour at −78° C. and then gradually returned to room temperature. The solution was extracted with saturated brine and CH$_3$CO$_2$Et. The organic layer obtained was dried with MgSO$_4$ and the solvent was distilled off. To the yellow residue obtained were added 50 mL of CH$_2$Cl$_2$ and 4 mL of H$_2$O$_2$, and the mixture was stirred for 3 hours in an ice bath. The reaction solution was extracted with saturated brine and dried with MgSO$_4$. The solvent was distilled off. The brown residue obtained was purified by silica gel column chromatography (CH$_2$Cl$_2$: hexane=4:1), yielding target compound 2 in the form of white crystals.

1,3,5-Tris(4-diphenylphosphorylphenyl)benzene (tppb): 2

Yield: 0.72 g (28%). $^1$H NMR (400 MHz, CDCl$_3$): δ 7.63-7.82 (m, 3H, Ar), δ 7.41-7.59 (m, 2H, Ar) ppm. EI-MS: m/z=906.26[M]$^+$. FTIR (ATR): 3080-3030 (ar C—H), 1610-1575 (ar C—C), 1190 (P=O). Elemental analysis: Calcd for C$_{60}$H$_{45}$O$_3$P$_3$.H$_2$O: C, 77.91; H, 5.12. Found: C, 78.32; H, 5.04.

Example 1

Complex Synthesis

Synthesis of [Eu(hfa)$_3$(tppb)]$_n$

[Chem. 15]

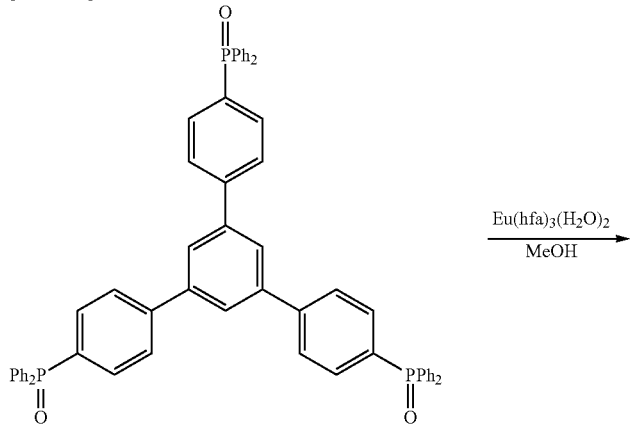

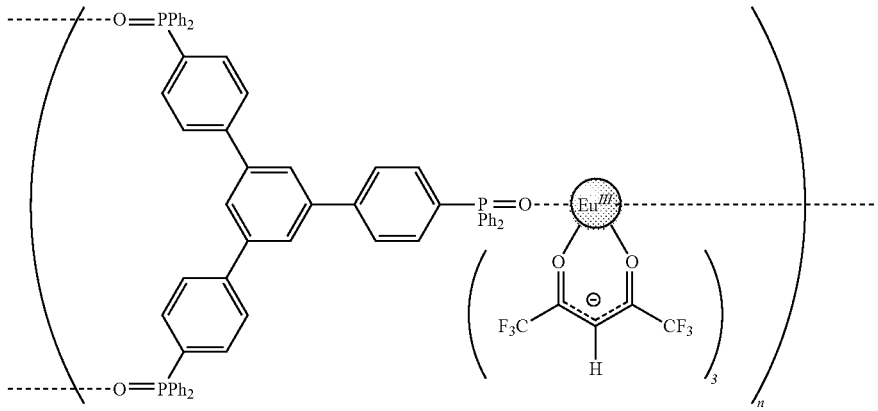

An 80 mg (0.09 mmol) quantity of tppb and 85 mg (0.11 mmol, 1.2 equiv) of Eu(hfa)$_3$(H$_2$O)$_2$ were dissolved in 7 mL of MeOH. The mixture was refluxed with heating for 6 hours at 60° C. The MeOH was distilled off under reduced pressure. The solid obtained was washed with chloroform and the impurities were removed by filtration. The solvent in the filtrate was distilled off under reduced pressure and the product was dried, yielding a pale yellow powder.

[Eu(hfa)$_3$(tppb)]$_n$: 3

Yield: 121 mg (92%). ESI-MS: m/z=1473.2[M]$^+$. FTIR (ATR): 3080-3030 (ar C—H), 1650 (P=O), 1625-1575 (ar C—C), 1300-1230 (C—F), 1190-1150 (P=O). Elemental analysis:

Sheet integrated-type Eu(III) complex [Eu(hfa)$_3$(tpptz)]$_n$ was synthesized according to the following scheme. Commercial products (Kanto Chemical, Tokyo Chemical Industry, Wako Pure Chemical Industries) were employed as the starting materials, catalysts, and solvents. Each compound was identified by $^1$H-NMR and ESI-Mass Spectrometry.

[Chem. 16]

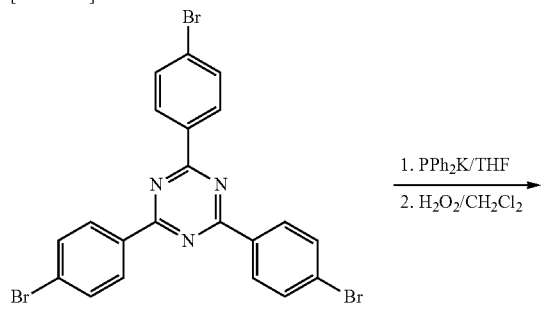

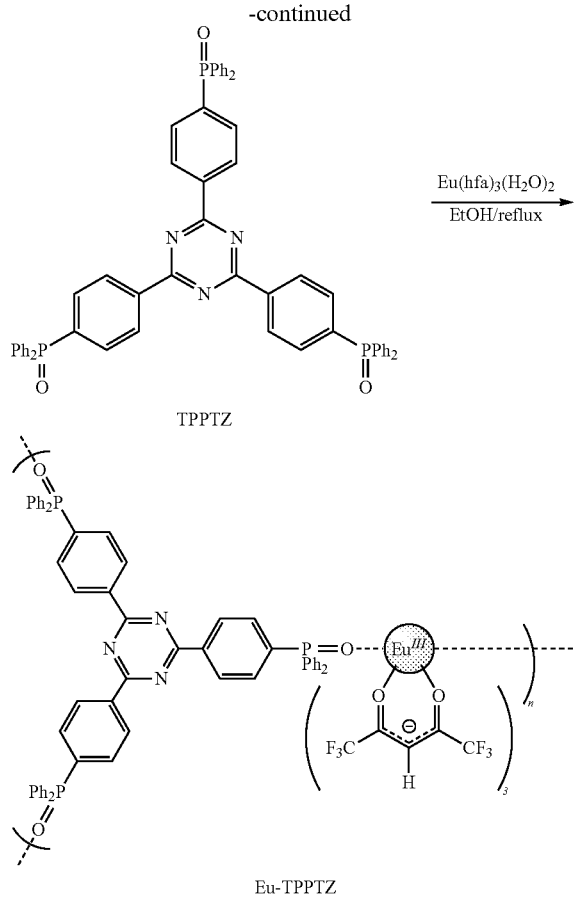

TPPTZ

Eu(hfa)₃(H₂O)₂
————————→
EtOH/reflux

Eu-TPPTZ

Reference Example 2: Ligand Synthesis

Synthesis of 2,4,6-Tris(4-bromophenyl)-1,3,5-triazine[4]

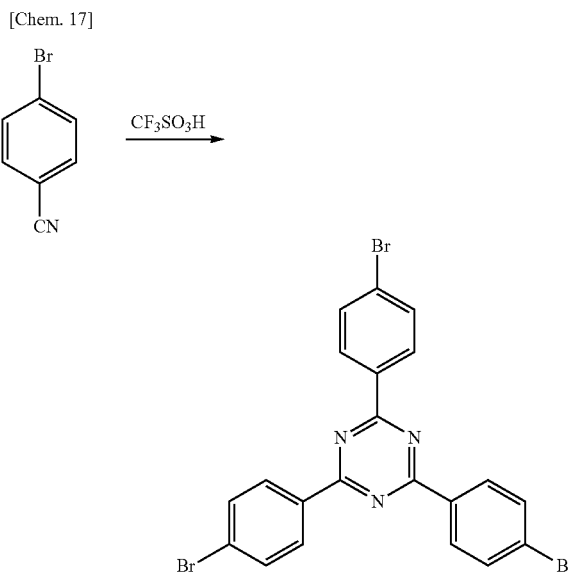

A 50 mL capacity two-necked flask was flame dried and backfilled with Ar. A 4.5 mL (50.85 mmol) quantity of trifluoromethanesulfonic acid was added dropwise. Subsequently, 2.75 g (14.0 mmol) of 4-bromobenzonitrile was added under an Ar flow and the mixture was stirred for 1 hr at 0° C. The mixture was then stirred overnight at room temperature. The orange reaction solution was poured into 0° C. distilled water to precipitate white crystals. Neutralization was conducted with NaOH aq, the precipitate was recovered by filtration, and the precipitate was washed several times with distilled water. The white crystals were dried at 80° C. under reduced pressure and then recrystallized from hot toluene, yielding acicular crystals.

Quantity obtained (yield): 1.27 g (50%)

$^1$H-NMR (400 MHz, CDCl$_3$): δ 8.54 (d, 6H, Ar), 7.72 (d, 6H, Ar) ppm.

Synthesis of 2,4,6-Tris(4-diphenylphosphorylphenyl)-1,3,5-triazine (tpptz)[4]

[Chem. 8]

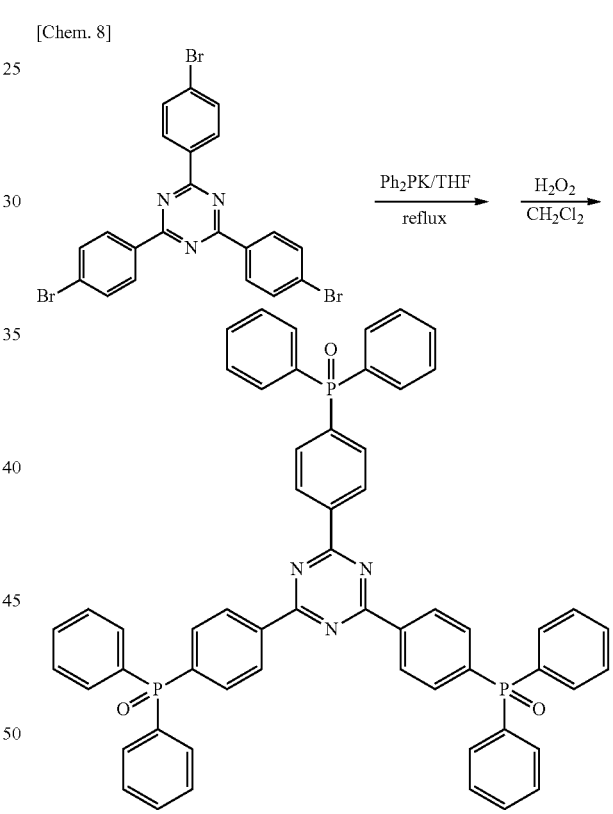

A 50 mL capacity two-necked flask was flame dried and then backfilled with Ar. A 0.295 g (0.5 mmol) quantity of 2,4,6-tris(4-bromophenyl)-1,3,5-triazine and 10 mL of dry THF were then added. A 3.5 mL (1.75 mmol, 3.5 equiv.) quantity of 0.5 M potassium diphenylphosphone in THF was then added with a dropping funnel and the mixture was refluxed for 48 hours. The reaction solution was returned to room temperature and extracted with CH$_2$Cl$_2$/NaCl aq. The organic layer was dried with MgSO$_4$ and the solvent was distilled off. When ether/hexane was added to the oily product obtained, fine crystals precipitated. These were recovered by suction filtration, yielding lustrous yellow crystals. To these crystals were added 30 mL of CH$_2$Cl$_2$ and 10 mL of $H_2O_2$, and the mixture was stirred for 4 hours. The reaction solution was extracted with $CH_2Cl_2$/NaCl aq, the organic layer was dried with $MgSO_4$, and the solvent was distilled off. The yellow oily residue obtained was vacuum dried, yielding white crystals.

Quantity produced (yield): 0.39 g (42%)

$^1$H NMR (400 MHz, $CDCl_3$): δ 8.8 (m, 6H, Ar), 7.89 (m, 6H, Ar), 7.74-7.43 (m, 30H, Ar) ppm. ESI-MS (m/z)=910.25 $[M+H]^+$.

Embodiment 2

Complex Synthesis

Synthesis of $[Eu(hfa)_3(TPPTZ)]_n$ (Eu-tpptz)

[Chem. 19]

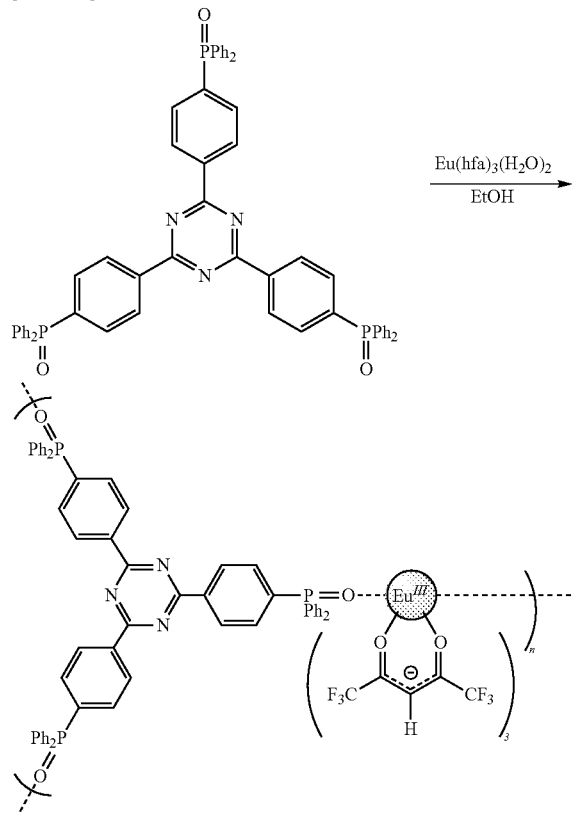

A 30 mg (0.03 mmol) quantity of tpptz and 81 mg (0.9 mmol, 3 equiv) of $Eu(hfa)_3(H_2O)_2$ were dissolved in 20 mL of EtOH and the mixture was refluxed with heating for 6 hours. The solvent was distilled off under reduced pressure. The white crystals obtained were washed with chloroform and recovered by suction filtration.

Quantity of Eu-tpptz produced (yield): 39.3 mg (70%)

ESI-MS (m/z)=1476.12 $[Eu(hfa)_2(tpptz)]^+$, 2249.49 $[Eu_2(hfa)_5(tpptz)]^+$, 3024.91 $[Eu_3(hfa)_8(tpptz)]^+$, 3933.07 $[Eu_3(hfa)_8(tpptz)_2]^+$.

Measurement of Photophysical Properties

The $[Eu(hfa)_3(tppb)]_n$ and $[Eu(hfa)_3(tpptz)]_n$ produced analyzed as follows.

Measurement of Absorption Spectra i) Measurement of Diffuse Reflection Absorption Spectra A JASCO V-670 integrating sphere was mounted, and the sample in the form of the complex was inserted at a height of 6 mm into a powder cell. A diffusion plate was employed as a reference. Measurement was conducted over a measurement range of 220-800 nm at a scan rate of 40 nm/min.

ii) Measurement of Absorption Spectra

A methanol solution ($1.0×10^{-5}$ M) of $[Eu(hfa)_3(tppb)]_n$ or $[Eu(hfa)_3(tpptz)]_n$ was prepared. A JASCO V-670 and 1×1 cm tetrahedral quartz cell were employed in measurement conducted over a measurement range of 220-800 nm at a scan rate of 200 nm/min.

Calculation of Quantum Emission Yield i) Calculation of Quantum Emission Yield by Ligand Excitation A JASCO FP-6600 integrating sphere was mounted, and the sample in the form of the complex and a reference in the form of $BaSO_4$ powder were inserted at a height of 6 mm into a powder cell. Measurement was conducted over a measurement range of 350-730 nm at an excitation wavelength of 370 nm and at the scan rate. The yield of light-emitting quantity by ligand excitation was calculated using equation (1) below by the absolute method.

$$\Phi_{tot} = \frac{\int I_{em}^{sam}(\tilde{v})d\tilde{v}}{\int [I_{ex}^{ref}(\tilde{v}) - I_{ex}^{sam}(\tilde{v})]d\tilde{v}} = \frac{Int}{Abs} \quad (1)$$

In the above equation, $\Phi_m$ denotes the yield [%] of europium quanta emission due to ligand excitation. In the numerator, I denotes the integrated intensity [–] of the light-emitting spectrum of the sample, and in the denominator, I denotes the integrated intensities [–] of the excitation spectra of the reference and the sample, respectively.

Initially, to calculate the amount of light absorbed, the area of the excitation spectrum obtained by exciting the complex with 370 nm light was subtracted from the area of the excitation spectrum obtained by exciting the $BaSO_4$ powder employed as reference with light at 370 nm. Next, to calculate the amount of light emitted, the total area of the emission band due to the $^5D_0 \rightarrow {^7F_J}$ transition (J=0-4) in the emission spectrum of the complex obtained was calculated. Dividing the amount of light emitted by the amount of light absorbed gave the quantum emission yield by ligand excitation.

ii) Calculation of Quantum Emission Yield by Direct Excitation

Using the same method as that used for ligand excitation, the quantum emission yield due to direct excitation was calculated for a measurement range of 550-730 nm and an excitation wavelength of 465 nm at the scan rate. The quantum emission yield due to direct excitation was calculated using equation (2)[3] below.

$$\Phi_{Ln} = \frac{\tau_{obs}}{\tau_{rad}} \quad (2)$$

$$\frac{1}{\tau_{rad}} = A_{MD,0} \cdot n^3 \cdot \left(\frac{I_{tot}}{I_{MD}}\right)$$

$$\eta_{sens} = \frac{\Phi_{tot}}{\Phi_{Ln}}$$

In the equations, $\Phi_{Ln}$ denotes the quantum emission yield of europium due to direct excitation, $\tau_{obs}$ denotes the emission lifetime observed, $A_{MD,0}$ is a constant with $A_{MD}$, o=14.65 s$^{-1}$, and n denotes the refractive index, which is normally 1.5 for coordination compounds in a solid state. ($I_{tot}/I_{MD}$) is the ratio of the integrated intensity of the entire emission spectrum in the $^5D_0 \rightarrow ^7F_J$ (J=0-4) transition to the integrated intensity in the $^5D_0 \rightarrow ^7F_1$ magnetic dipole transition. $\eta_{sens}$ is the efficiency of energy displacement from ligands to europium.

Measurement of Emission Lifetime

[Eu(hfa)$_3$(tppb)]$_n$ powder was secured between glass slides and measurement was conducted. The excitation light source employed was a Spectra-Physics YAG laser head (H-INDI2-LW). The response to the YAG laser was measured with a digital oscilloscope (TDS3052B) made by Japan Tektronix. The emission lifetime $\tau_{obs}$ that was obtained was calculated from the slope of a straight line obtained by plotting the the vertical axis value of the emission decay profile as a natural log.

REFERENCES

[1] M. Stol, D. J. M. Snelders, H. Kooijman, A. L. Spek, G. P. M. Klink and G. Koten, *Dalton Trans.*, 2007, 2589-2593.
[2] I. O. Koshevoy, L. Koskinen, E. S. Smirnova, M. Haukka, T. A. Pakkanen, A. S. Melnikov, and S. P. Tunik, *Z. Anorg. Allg. Chem.* 2010, 636, 795-802.
[3] S. V. Eliseeva, D. N. Pleshkov, K. A. Lyssenko, L. S. Lepnev, J-C. G. Bunzli, and N. P. Kuzmina. *Inorg. Chem.* 2011, 50, 5137-5144
[4] N. P. Kuzmina. *Inorg. Chem.* 2011, 50, 5137-5144

Photophysical Characteristics of [Eu(hfa)$_3$(tppb)]$_n$

1 Measurement of Absorption Spectrum

Figure 2:
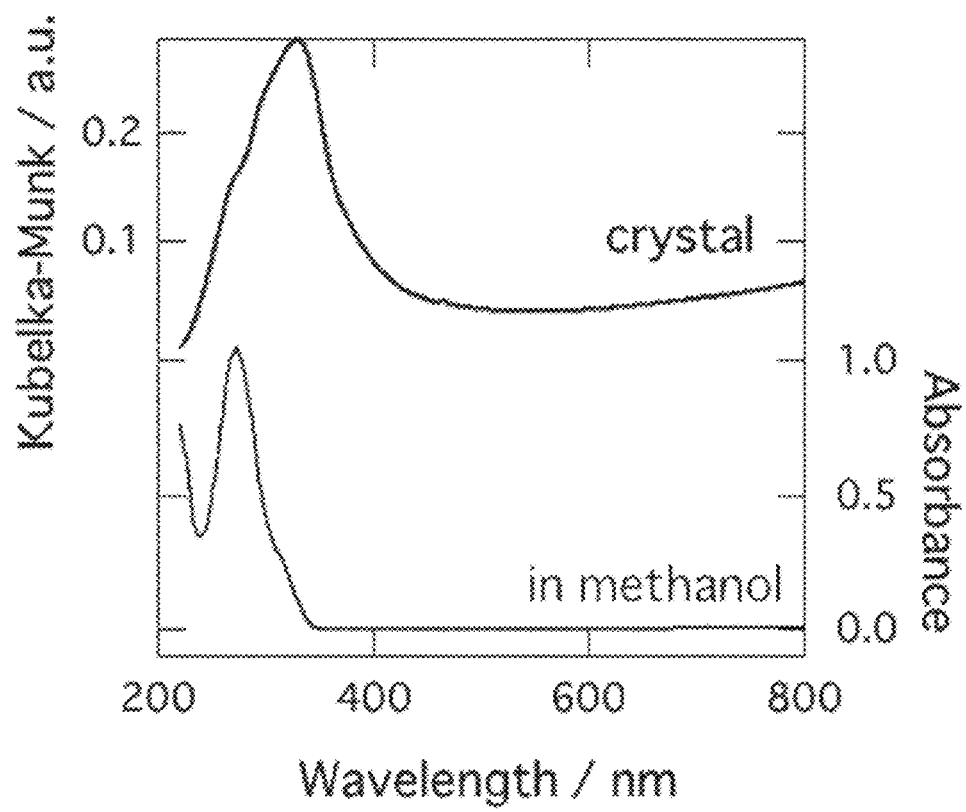
FIG. 2 shows the absorption spectrum (red) in methanol of [Eu(hfa)$_3$(tppb)]$_n$ and the diffuse reflection absorption spectrum (black) thereof in a solid state.

FIG. 2 shows the diffuse reflection absorption spectrum in a solid state and absorption spectrum in methanol of [Eu(hfa)$_3$(tppb)]$_n$.

The rough forms of the two spectra differ greatly. [Eu(hfa)$_3$(tppb)]$_n$ was thus found to adopt different structures in a solid state and in solution. The absorption band due to the π-π* transition of hfa at 270 nm in both a solid and in methanol solution was reviewed. The small band at 465 nm corresponds to the $^5D_0 \rightarrow ^7F_2$ transition of Eu(III) ions. In the solid state, a unique absorption band was observed in the vicinity of 330 nm that was not seen in methanol solution. This was an absorption band called the inter-ligand charge transfer (ILCT) band. It is thought to be a shift to a longer wavelength than the original absorption of hfa for stabilization by means of a charge redistribution between hfa ligands. Because the CT transition is permissible according to Laporte, great absorption is exhibited. Because this band appears in a solid state, it is thought that [Eu(hfa)$_3$(tppb)]$_n$ molecules, which assume a planar structure in the solid state, become a polymer in which the sheets adopt a stacked form due to weak bonds resulting from some interaction between molecules, such as hfa hydrogen bonds.

2 Measurement of Emission Spectra

Figure 3:
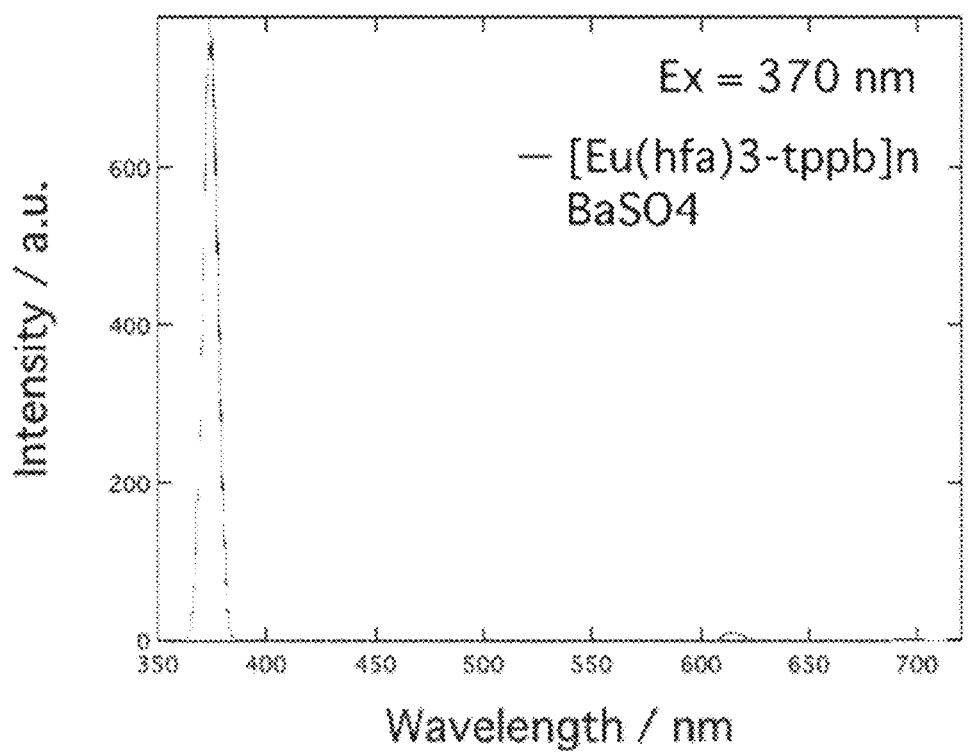
FIG. 3 shows the light emission spectrum (395 nm excitation) of [Eu(hfa)$_3$(tppb)]$_n$.
Figure 4:
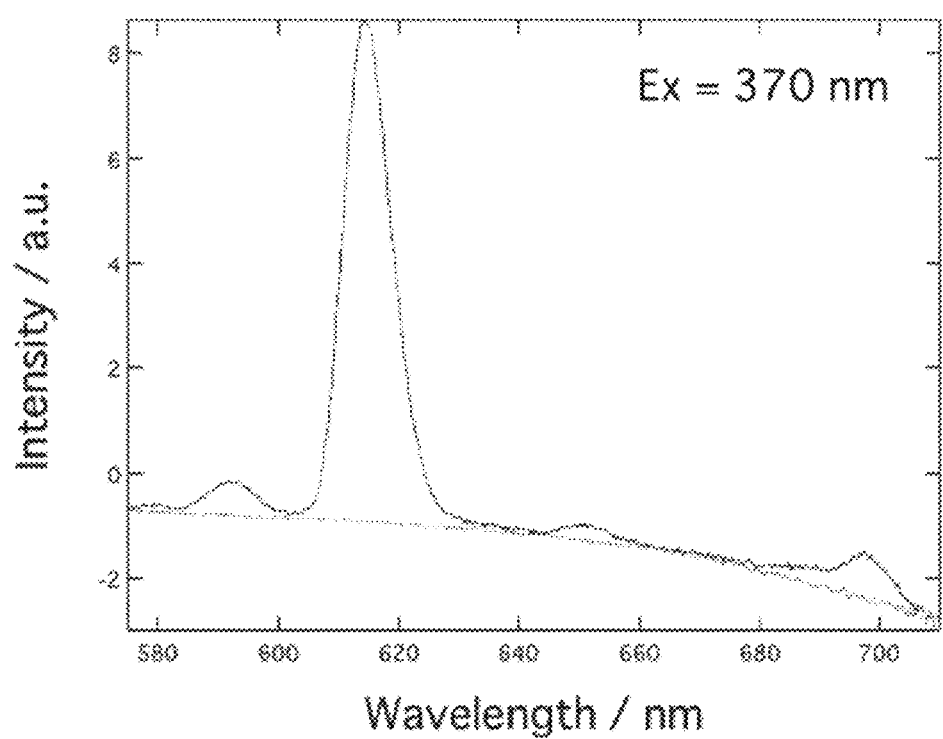
FIG. 4 shows an enlarged view of the emission spectrum of [Eu(hfa)$_3$(tppb)]$_n$.
Figure 5:
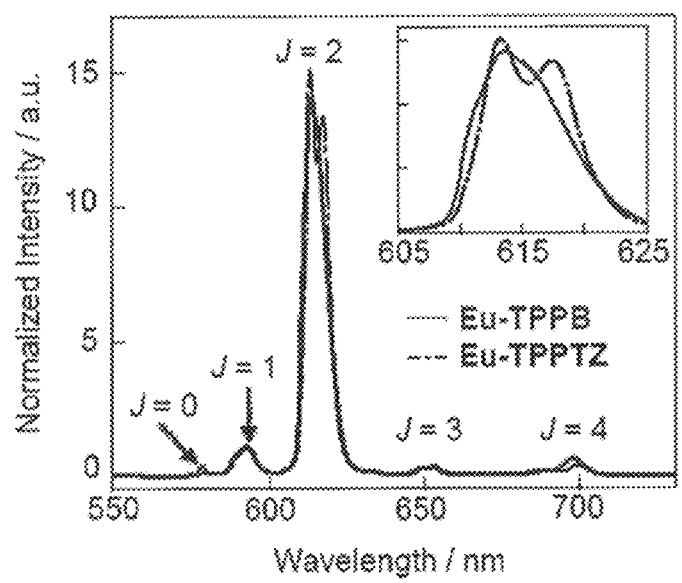
FIG. 5 shows light emission spectra (465 nm excitation) of [Eu(hfa)$_3$(tppb)]$_n$ and [Eu(hfa)$_3$(tpptz)]$_n$.

FIGS. 3 and 4 show the emission spectra of [Eu(hfa)$_3$(tppb)]$_n$ due to 395 nm excitation (ligand excitation). FIG. 5 shows the emission spectra (465 nm excitation) of [Eu(hfa)$_3$(tppb)]$_n$ and [Eu(hfa)$_3$(tpptz)]$_n$. In both the ligand excitation and direct excitation emission spectra, based on the 4f-4f electron transition that is characteristic of Eu(III) complexes, 578 nm ($^5D_0 \rightarrow ^7F_0$), 592 nm ($^5D_0 \rightarrow ^7F_1$), 614 nm ($^5D_0 \rightarrow ^7F_2$), 650 nm ($^5D_0 \rightarrow ^7F_3$), and 700 nm ($^5D_0 \rightarrow ^7F_4$) emission was observed.

3 Measurement of Quantum Emission Yield and Emission Lifetime

Figure 6:
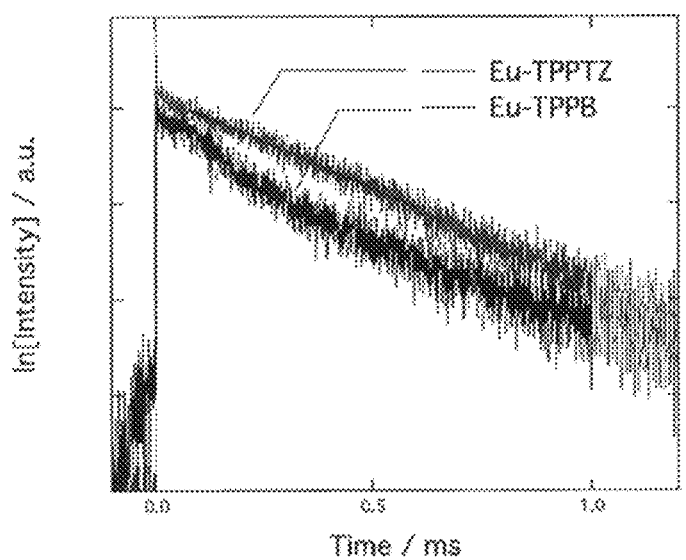
FIG. 6 shows the light-emission lifetimes of [Eu(hfa)$_3$(tppb)]$_n$ and [Eu(hfa)$_3$(tpptz)]$_n$ in a solid state.
Figure 7:
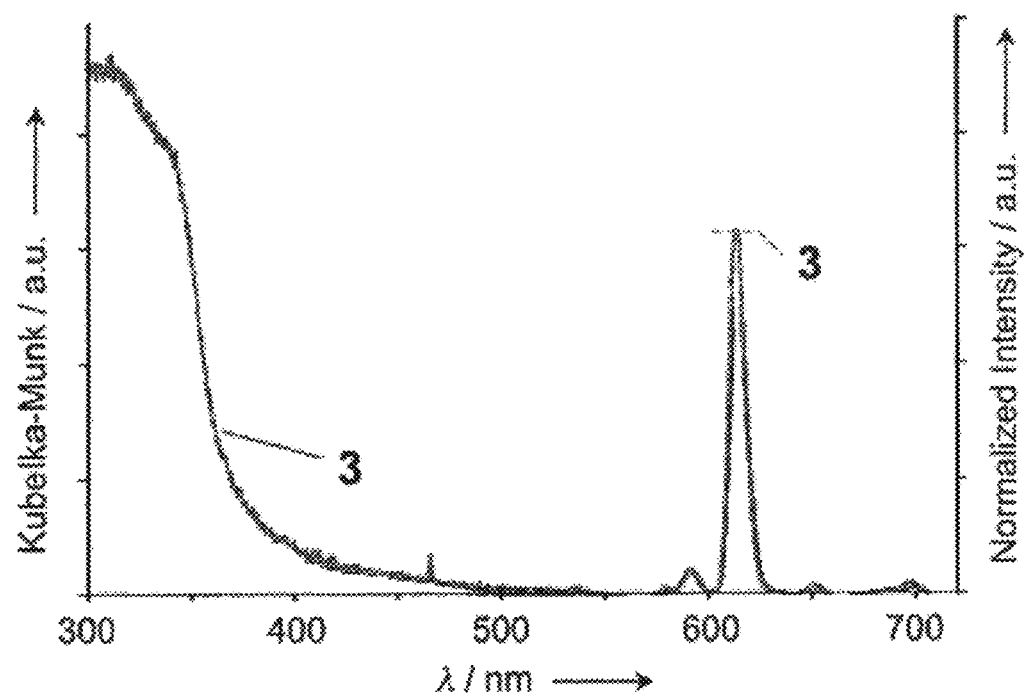
FIG. 7 shows the absorption spectrum (line 3) of [Eu(hfa)$_3$(dppcz)]$_n$, the polymer complex of Nonpatent Reference 1.

FIG. 6 and Table 1 give the results of measurement of the quantum emission yield ($\Phi_{Ln}$) due to direct excitation (465 nm), the quantum emission yield ($\Phi_{tot}$) due to ligand excitation (370 nm), the emission lifetime (τobs), the energy transfer efficiency ($\eta_{sens}$), the radiation rate constant ($k_r$), and the no radiation rate constant ($k_{nr}$) for [Eu(hfa)$_3$(tppb)]$_n$ and [Eu(hfa)$_3$(tppb)]$_n$, as well as a conventional complex in the form of Eu(hfa)$_3$(biphepo). Further, the various physical properties of [Eu(hfa)$_3$(dppcz)]$n$, which is the polymer complex of Nonpatent Reference 1 were posted to Table 1 and the absorption spectra was posted to FIG. 7 (line 3). The fluorescence lifetime is normally given in units of ns. Thus, the emission of [Eu(hfa)$_3$(tppb)]$_n$ was found to exhibit an extremely long lifetime, although inferior to that of Eu(hfa)$_3$(biphepo), indicating strong emission characteristics. Compared to Eu(hfa)$_3$(biphepo), $\Phi_{Ln}$, $\tau_{obs}$, and $k_r$ were lower. The reason why $k_{nr}$ was a high value was attributed to the fact that lower vibration was not reflected because of higher symmetry of structure than Eu(hfa)$_3$(biphepo). However, [Eu(hfa)$_3$(tppb)]$_n$ was found to have a $\eta_{sens}$ value that was much higher than that of Eu(hfa)$_3$(biphepo). This was attributed to the ILCT band observed in the absorption spectrum measurement shown in FIG. 2. Compared to the polymer complex [Eu(hfa)$_3$(tppcz)]$_n$ of Nonpatent Reference 1, [Eu(hfa)$_3$(tppb)]$_n$ had a high $\eta_{sens}$. This was in conformity with the fact that no ILCT band was observed in the absorption spectrum of the polymer complex of Nonpatent Reference 1 shown in FIG. 7. [Eu(hfa)$_3$(tpptz)]$_n$ exhibited higher values of $\tau_{obs}$, $\Phi_{Ln}$, $\Phi_{tot}$, and $\Phi_{sens}$ than Eu(hfa)$_3$(biphepo).

TABLE 1

Optical property data of Eu(III) complexes (solid)

| Complex | $\tau_{obs}$ [ms] | $\Phi_{Ln}$ [%]$^a$ | $\Phi_{tot}$ [%]$^b$ | $\eta_{sens}$ [%]$^c$ | $k_r$ [s$^{-1}$]$^d$ | $k_{nr}$ [s$^{-1}$]$^e$ |
|---|---|---|---|---|---|---|
| [Eu(hfa)$_3$(tppb)]$_n$ | 0.82 | 55 | 44 | 80 | 5.4 × 10$^2$ | 6.8 × 10$^2$ |
| Eu(hfa)$_3$(biphepo) | 0.94 | 73 | 21 | 29 | 7.8 × 10$^2$ | 2.8 × 10$^2$ |
| [Eu(hfa)$_3$(dppcz)]$_n$ | 0.93 | 83 | 53 | 64 | 8.9 × 10$^2$ | 1.8 × 10$^2$ |
| [Eu(hfa)$_3$(tpptz)]$_n$ | 0.95 | 89 | 31 | 35 | | |

Figure 8:
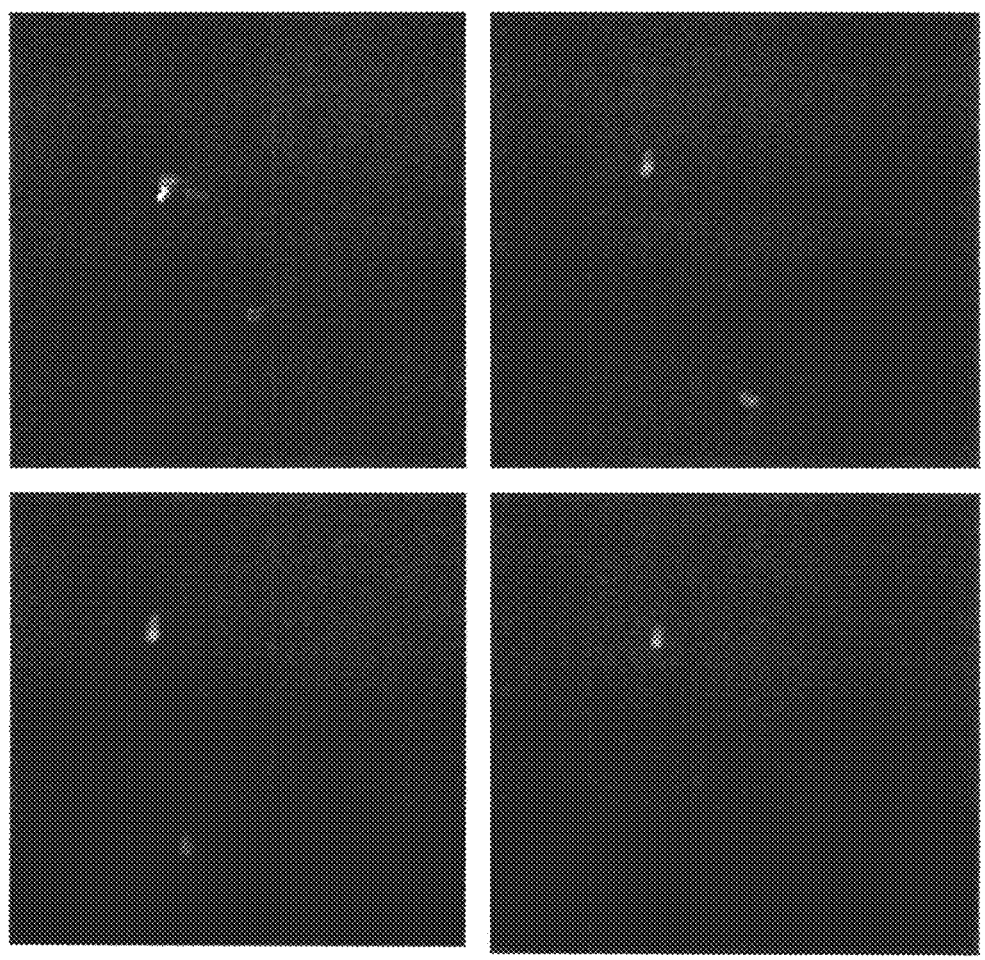
FIG. 8 shows the triboluminescence of [Eu(hfa)$_3$(tppb)]n.

$^a$Based on equation (1);
$^{b,c}$based on equation (2);
$^d k_r = \Phi_{Ln}/\tau_{obs}$;
$^e = 1/\tau_{obs} - k_r$ 4 Measurement of Triboluminescence and Emission Spectra Thereof When the crystals of [Eu(hfa)$_3$(tppb)]$_n$ were pulverized, intense red triboluminescence derived from Eu(III) ions was observed (FIG. 8).

Based on ESI-MS results, [Eu(hfa)$_3$(tppb)]$_n$ was found to be present as a monomer in solution with a ratio of ligands and Eu(III) ions of 1:1. Based on measurement of the diffuse reflection absorption spectra in a solid state and the absorption spectra in methanol solution of [Eu(hfa)$_3$(tppb)]$_n$, because it had absorption due to the ILCT band in a solid state, [Eu(hfa)$_3$(tppb)]$_n$ was thought to adopt the structure of a stacked sheet polymer due to some interaction, such as hydrogen bonds, in the solid state.

Figure 9:
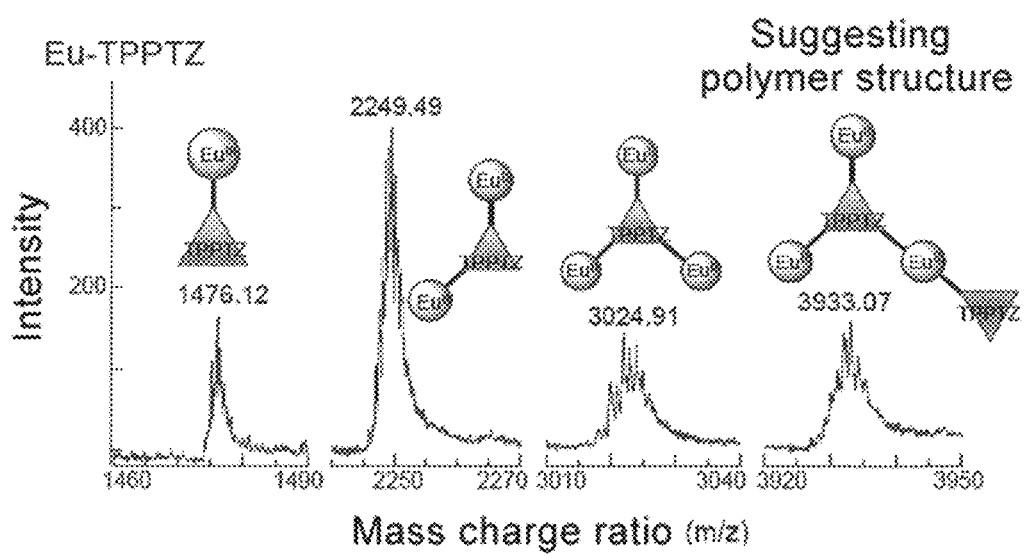
FIG. 9 shows a spectrum of [Eu(hfa)$_3$(tpptz)]$_n$ obtained by electrospray ionization mass spectrometry (ESI-MS).
Figure 10:
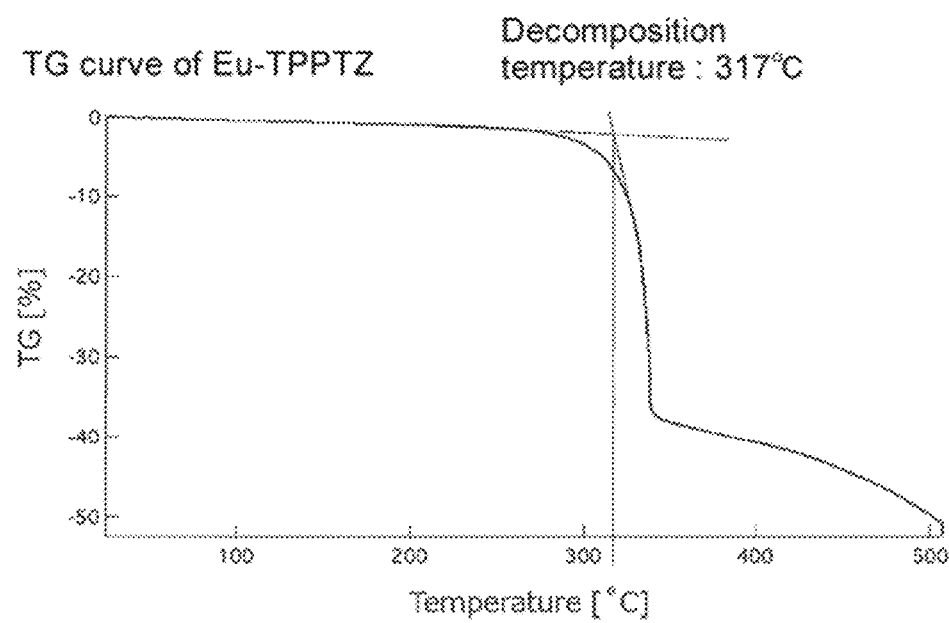
FIG. 10 shows a TG curve of [Eu(hfa)$_3$(tpptz)]$_n$.

The ESI-MS results for [Eu(hfa)$_3$(tpptz)]$_n$ given in FIG. 9 suggest the presence of a polymer structure for [Eu(hfa)$_3$(tpptz)]$_n$. The TG curve shown in FIG. 10 gives the decomposition temperature of [Eu(hfa)$_3$(tpptz)]$_n$ as 317° C., indicating considerable thermal stability.

With regard to emission characteristics, [Eu(hfa)$_3$(tppb)]$_n$ exhibited intense red light emission due to a photosensitizing effect of the ligands with 370 nm excitation. In quantum emission yield measurement and emission lifetime measurement, both [Eu(hfa)$_3$(tppb)]$_n$ and [Eu(hfa)$_3$(tpptz)]$_n$ exhibited extremely high energy transfer efficiency relative to the conventional complex, which was attributed to the ILCT band.

Pulverizing [Eu(hfa)$_3$(tppb)]$_n$ crystals and [Eu(hfa)$_3$(tpptz)]$_n$ crystals was found to bring about intense red triboluminescence derived from Eu(III).

INDUSTRIAL APPLICABILITY

The present invention is useful in fields relating to luminescent materials.

The invention claimed is:

1. A rare earth complex having a crosslinked structure, comprising (a) phosphine oxide compounds each denoted by formula (1):

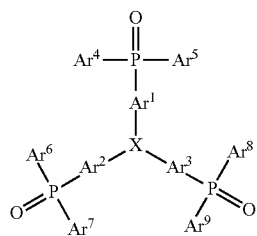
(1)

where X denotes an atom having three-fold symmetry in a plan view of the chemical structural formula containing the connectors of the atom, or a group of atoms having three-fold symmetry in a plan view of the chemical structural formula, wherein the group of atoms is an aryl group which may comprise one or more substituents, or a heteroaryl group which may comprise one or more substituents;

where each of Ar$^1$ to Ar$^9$ independently denotes an aryl group which may comprise one or more substituents;

(b) rare earth ions selected from the group consisting of Ce, Pr, Nd, Pm, Sm, Eu, Gd, Tb, Dy, Ho, Er, Tm, Yb and Lu; and (c) diketo compounds each denoted by formula (2);

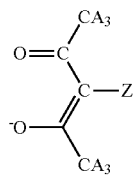
(2)

where A independently denotes a hydrogen atom, an alkyl group with 1 to 6 carbon atoms, or a halogen atom, and Z denotes a hydrogen atom or a deuterium atom;

wherein a coordination number of the diketo compound and the phosphine oxide compound relative to the rare earth ions is 8 to 10;

wherein each of three phosphine oxide groups of the phosphine oxide compound bonds to a different rare earth ion whereby the phosphine oxide compounds and the rare earth ions form a crosslinked structure.

2. The complex according to claim 1, wherein the group of atoms is an aryl group or a heteroaryl group.

3. The complex according to claim 1, wherein each of Ar$^1$ to Ar$^9$ denotes a phenyl group which may comprise one or more substituents.

4. The complex according to claim 1, wherein the diketo compound is at least one compound selected from the group consisting of acetyl acetone (acac), 2,2,6,6-tetramethylheptane-3,5-dione (TMHD), 1,1,1-trifluoroacetylacetone (TFA), and 1,1,1,5,5,5-hexafluoroacetylacetone (HFA).

5. The complex according to claim 1, wherein the phosphine oxide compound denoted by formula (1) is at least one compound selected from the group consisting of (1-1) to (1-3) below:

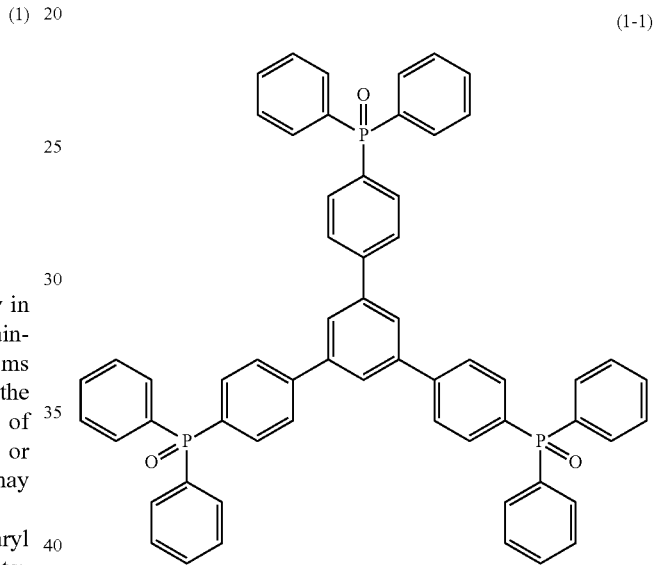
(1-1)

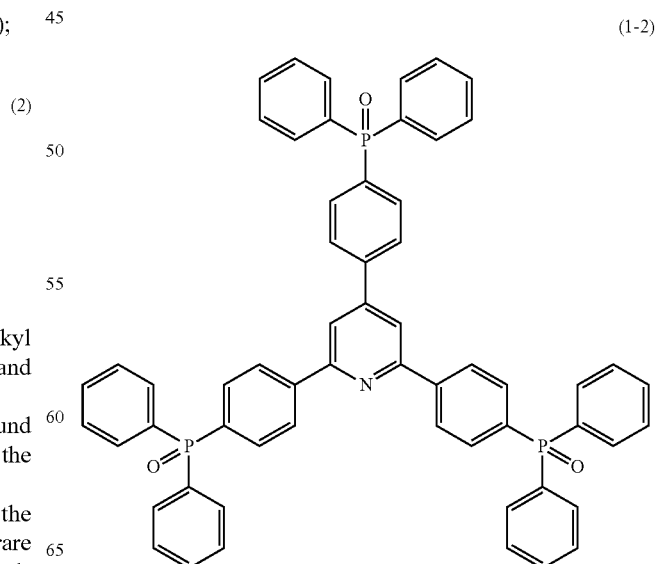
(1-2)

-continued (1-3)

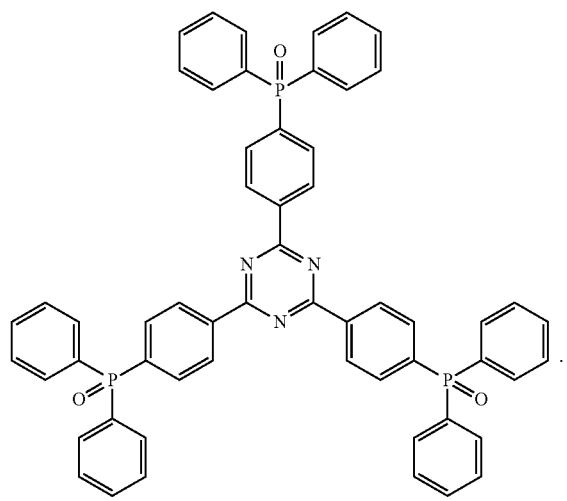

(1-5)

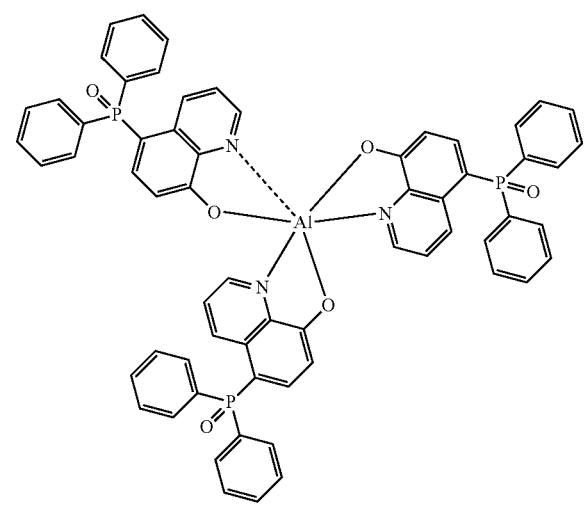

6. The complex according to claim 1, wherein the plurality of rare earth complexes having a crosslinked structure has an integrated sheet structure.

7. A light-emitting element comprising a light-emitting material, wherein the light-emitting material comprises the complex having a crosslinked structure according to claim 1.

8. A luminescent ink composition comprising the complex having a crosslinked structure according to claim 1 and a binder.

9. A luminescent plastic composition comprising the complex having a crosslinked structure according to claim 1 and a plastic material.

10. The complex according to claim 1, wherein the crosslinked structure spreads out in planar fashion and the repetition number in the crosslinked structure falls within a range of 2 to 10,000.

11. The complex according to claim 1, wherein the molecular weight of the rare earth complex having a crosslinked structure falls within a range of 1,000 to 1,000,000.

12. A rare earth complex having a crosslinked structure, comprising (a) phosphine oxide compounds each denoted by formula (1-4) or (1-5):

(1-4)

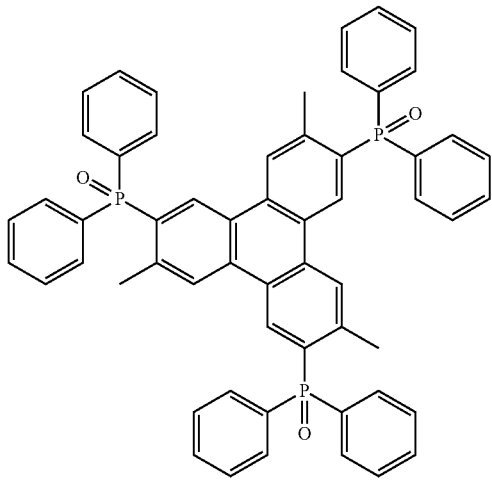

(b) rare earth ions selected from the group consisting of Ce, Pr, Nd, Pm, Sm, Eu, Gd, Tb, Dy, Ho, Er, Tm, Yb and Lu; and (c) diketo compounds each denoted by formula (2):

(2)

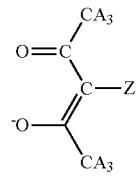

where A independently denotes a hydrogen atom, an alkyl group with 1 to 6 carbon atoms, or a halogen atom, and Z denotes a hydrogen atom or a deuterium atom;

wherein a coordination number of the coordination compound and the phosphine oxide compound denoted by formula (1-4) or (1-5) relative to the one or more rare earth ions is 8 to 10;

wherein each of three phosphine oxide groups of the phosphine oxide compound of formula (1-4) or (1-5) bonds to a different rare earth ion whereby the phosphine oxide compounds denoted by formula (1-4) or (1-5) and the rare earth ions have a crosslinked structure.

* * * * *